(12) United States Patent
Kuo

(10) Patent No.: US 11,730,635 B2
(45) Date of Patent: Aug. 22, 2023

(54) ABSORBENT ARTICLE, ENCLOSING PANTS, AND METHOD FOR WEARING COMBINATION THEREOF

(71) Applicant: KANGCHENG INTERNATIONAL CO., LTD., New Taipei (TW)

(72) Inventor: Shih-Huey Kuo, New Taipei (TW)

(73) Assignee: KANGCHENG INTERNATIONAL CO., LTD., New Taipei (TW)

( * ) Notice: Subject to any disclaimer, the term of this patent is extended or adjusted under 35 U.S.C. 154(b) by 603 days.

(21) Appl. No.: 16/815,020

(22) Filed: Mar. 11, 2020

(65) Prior Publication Data
US 2020/0315863 A1 Oct. 8, 2020

(30) Foreign Application Priority Data

Apr. 2, 2019 (CN) .......................... 201910263106.3

(51) Int. Cl.
| | | |
|---|---|---|
| *A61F 13/491* | (2006.01) | |
| *A61F 13/494* | (2006.01) | |
| *A61F 5/453* | (2006.01) | |
| *A61F 13/62* | (2006.01) | |

(Continued)

(52) U.S. Cl.
CPC ........ *A61F 13/4915* (2013.01); *A61F 5/4401* (2013.01); *A61F 5/453* (2013.01); *A61F 13/496* (2013.01); *A61F 13/49473* (2013.01); *A61F 13/622* (2013.01)

(58) Field of Classification Search
CPC .... A61F 13/4915; A61F 5/4401; A61F 5/453; A61F 13/49473; A61F 13/496; A61F 13/622; A61F 13/505; A61F 5/4404; A61F 13/49009; A61F 13/49011; A61F 13/49058; A61F 13/49406; A61F 13/515; A61F 13/5655; A61F 13/74; A61F 13/66–80;
(Continued)

(56) References Cited

U.S. PATENT DOCUMENTS

| | | | | |
|---|---|---|---|---|
| 1,560,890 A | * | 11/1925 | Whitlock ................ | A61F 13/70 |
| | | | | 604/401 |
| 1,664,626 A | * | 4/1928 | Ito .......................... | A61F 13/64 |
| | | | | 604/397 |

(Continued)

FOREIGN PATENT DOCUMENTS

GB 2540151 A * 1/2017 ............... A41B 9/00

*Primary Examiner* — Nicholas J. Weiss
*Assistant Examiner* — Gabriella E Burnette
(74) *Attorney, Agent, or Firm* — Leong C. Lei

(57) ABSTRACT

An absorbent article and enclosing pants and a method for wearing the combination thereof are provided. The absorbent article has a front lifting section and a rear lifting section that are provided with apertures to allow male and female parts of hook-and-loop fasteners of the enclosing pants to touch inside the apertures and to engage outside the apertures for preventing skidding. An isolating absorbent article may have an easy tear line opening for selectively tearing and tightly surrounding around a rear root portion of the scrotum to isolate the external sex organ and for installation or extension of a urine tube or a urine sack. The enclosing pants has the front pad and a rear pad having two lifting and looping sections and a central opening section, the central opening for fixing and correspond the easy tear line opening.

20 Claims, 22 Drawing Sheets

(51) Int. Cl.
*A61F 5/44* (2006.01)
*A61F 13/496* (2006.01)

(58) Field of Classification Search
CPC ...... A61F 5/44–4401; A61F 2005/4402; A61F 13/471
See application file for complete search history.

(56) References Cited

U.S. PATENT DOCUMENTS

| | | | | |
|---|---|---|---|---|
| 3,420,236 | A * | 1/1969 | De Woskin | A61F 13/76 604/398 |
| 3,635,221 | A * | 1/1972 | Champaigne, Jr. | A61F 13/505 604/394 |
| 3,900,032 | A * | 8/1975 | Heurlen | A61F 13/505 604/397 |
| 4,280,230 | A * | 7/1981 | LaFleur | A61F 13/70 2/408 |
| 4,315,508 | A * | 2/1982 | Bolick | A61F 13/49011 604/374 |
| 4,338,939 | A * | 7/1982 | Daville | A61F 5/4401 604/399 |
| 4,955,880 | A * | 9/1990 | Rodriquez | A61F 13/74 604/393 |
| 5,019,068 | A * | 5/1991 | Perez | A61F 13/49004 604/401 |
| 5,135,522 | A * | 8/1992 | Fahrenkrug | A61F 13/64 604/401 |
| 5,700,256 | A * | 12/1997 | Yamamoto | A61F 13/4752 604/397 |
| 5,707,364 | A * | 1/1998 | Coates | A61F 13/622 604/385.01 |
| 5,876,395 | A * | 3/1999 | Hart | A61F 13/505 604/394 |
| 6,432,098 | B1 * | 8/2002 | Kline | A61F 13/493 604/385.03 |
| 7,122,022 | B2 * | 10/2006 | Drevik | A61F 13/82 604/385.03 |
| 7,156,834 | B2 * | 1/2007 | Kawata | A61F 13/64 604/387 |
| 8,235,963 | B2 * | 8/2012 | Lodge | A61F 13/76 604/385.27 |
| 8,343,126 | B2 * | 1/2013 | Lodge | A61F 13/64 604/385.27 |
| 8,679,085 | B2 * | 3/2014 | Ronstrom | A61F 13/68 604/397 |
| 9,211,220 | B2 * | 12/2015 | Schambon | A61F 13/72 |
| 9,333,127 | B1 * | 5/2016 | Horsley | A61F 13/505 |
| 9,387,138 | B2 * | 7/2016 | Roe | A61F 13/5633 |
| 9,592,165 | B2 * | 3/2017 | Labit | A61F 13/505 |
| 10,004,649 | B2 * | 6/2018 | Kuo | A61F 13/49006 |
| 10,660,805 | B2 * | 5/2020 | Kuo | A61F 13/4915 |
| 11,147,722 | B2 * | 10/2021 | Zhou | A61F 13/8405 |
| 2001/0041879 | A1 * | 11/2001 | Karami | A61F 13/49 604/389 |
| 2004/0082933 | A1 * | 4/2004 | Karami | A61F 13/5644 604/393 |
| 2005/0148982 | A1 * | 7/2005 | Van Gompel | A61F 13/495 604/385.22 |
| 2012/0010585 | A1 * | 1/2012 | Labit | A61F 13/493 604/372 |
| 2012/0116339 | A1 * | 5/2012 | Labit | A61F 13/493 604/385.01 |
| 2014/0221954 | A1 * | 8/2014 | Wang | A61F 13/505 604/385.14 |
| 2017/0007474 | A1 * | 1/2017 | Kuo | A61F 13/4906 |
| 2018/0207038 | A1 * | 7/2018 | Kuo | A61F 13/505 |
| 2020/0315863 | A1 * | 10/2020 | Kuo | A61F 5/4401 |
| 2021/0145663 | A1 * | 5/2021 | Hayden | A61F 13/565 |

* cited by examiner

ABSORBENT ARTICLE, ENCLOSING PANTS, AND METHOD FOR WEARING COMBINATION THEREOF

TECHNICAL FIELD OF THE INVENTION

The present invention relates generally to an incontinence diaper, a combination of diaper and enclosing pants and a method for wearing the combination, with the primary purposes being environment protection and economics.

DESCRIPTION OF THE PRIOR ART

A known adult diaper is a fully coverage style having a generally "I" shape (i.e. flat diapers, which are fixed by the waist adhesive for wearing on body). One drawback is the size range is excessively large, such as an M size of a specific brand may be fit to waist size of 28-44 inches, and an L size can be fit to waist size of 38-62 inches, making it not closely attach to the body for most of the people and easily resulting in side leaking. A second drawback is that for a female wearer or a urine tube or urine sack (which is a flexible urine collection device for direct fitting to an outside surface of a penis) user, unnecessary consumable material used in the front belly section may cause waste of material and deterioration of the environment. A third drawback is that for a long-term bed lying person, enema must be taken for every three days in order to prompt defecating and this result in successive release of watery feces, which are made in a situation that the amount of the first day is the greatest and those of the second and third days are minor or just a tiny amount. Wearing such a known full-coverage diaper make causing the external sex organ to immerse in feces in the first day and leading to diaper rash, urinary tract infection, and subsequent medication care problems, and may easily cause side leaking (due to watery feces flowing and extending along hips); and in the second and third days, only a minor amount of leaking but the enter diaper must be disposed of, this leading to a waste. A fourth drawback is that the known diapers are of a large size and a great weight, so as to increase the costs of packaging, warehousing, shipping, waste processing, space, and caring, and thus causing a great burden for the family member.

Further, the urine tube is easy to entangle and may be pulled to detach, leading to leaking of urine. The urine sack shows great advantages for non-invasion observation of urine collection, caring attending, and environmental protection and is thus widely used. However, when the diaper is worn, the urine sack may be compressed to cause frequent reversal flowing or overflowing of urine, making it necessary for constantly and repeatedly cleaning, and in addition, a full coverage arrangement may lead to stuffing and high temperature, readily causing stinking and pollution of the surroundings.

A patent document that is known is Taiwan Utility Model TWM554341, which discloses material saving clothing (also by the present inventor) and is similarly published in countries worldwide, including China, Japan, and Europe. Although the known art also provides a combination of an absorbent article and a lifting and looping member (namely enclosing pants of this invention), a U-shaped notch that is completely cut open is different from an easy tear line opening taught in this invention that is an isolating structure that allows tightly surrounding a root of the scrotum after being torn open. Although the known art is arranged to expose a male external sex organ, a shielding style lifting and looping member is used for covering, making it not possible to install a urine sack. Although the known art allows a urine tube to extend, skidding-preventing glue (which requires additional operation for coating and thus increasing cost) must be applied to prevent undesired skidding, it is not achieved through combining a front pad and a rear pad to feature multiple purposes of ventilation, retention of a urine tube, retention of a urine sack, and adjusting fastening location.

A patent document of Japan Patent Publication 2005-124594 is also known, disclosing a diaper of which a front belly section is provided with a zipper based opening, which is openable for replacement of an absorbent pad and re-closable for covering, however, it is different from the structure of an easy tear line opening that is selectively opened and not re-closed.

SUMMARY OF THE INVENTION

An objective of the present invention is to provide an absorbent article, which is wearable in combination with the enclosing pants (meaning the absorbent article is not provided for wearing independently), the absorbent article being developed, according to the definition of environmental conservation, for saving of resources, repeated uses, and reduction of waste and also for achieving, under the condition of reducing basic materials, core materials, and elastic elements, the purposes of convenience and safety and cooling and comfortableness, so as to realize environmental protection, wherein an isolating absorbent article (1) and a shielding absorbent article (3) are provided, including front and rear lifting films that are provided with apertures to allow hook-and-loop fasteners of the enclosing pants to respectively touch inside the apertures and engage outside the apertures to prevent skidding and peeling and eliminating the need for position alignment, penetration through holes, and also eliminating the need for identifying directions in detaching.

Further, to prevent a male external sex organ from immersing in feces and urine and to overcome the drawbacks of the prior art diapers (which require entirely replaced even just seeping with a minor amount and so on), the isolating absorbent article (1) is structured such that an absorbent core front end is extended to form two projecting portions for absorbing watery feces flowing along hips and a recessed portion is formed between the two projecting portions and is provided with an easy tear line opening extending in a direction toward a belly for being selectively torn open and then tightly surrounded around a rear root portion of the scrotum to isolate the external sex organ for use by a bed-lying person or a sleeping person that wears a urine tube or a urine sack and for being selectively used by a female in sleeping or a wearer requiring hemodialysis (blood dialysis). Due to be usable by male and female wearers, saving of manufacturing machinery and space, reduction of fabrication, marketing, and management can be achieved.

Further, the shielding absorbent article (3) is provided for use by person in activity, which comprises a front belly section having a film that is provided with an easy tear line opening extending around an outer circumference of a front belly section of an absorbent core, in order to readily tear open and fold downward to install a urine sack in a nighttime (helping a frequent micturition person to sleep calmly) or to ventilate (improving stuffing or sweating and humid condition) and also for use by a person wearing no urine tube in a condition of being not torn open so as to save material and prevent side leaking.

To achieve the above objective, a technical solution adopted in this invention is an absorbent article, which comprises a liquid permeable top layer, a liquid impermeable bottom layer, an absorbent core disposed between the liquid permeable top layer and the liquid impermeable bottom layer, and a leaking protection barrier extending in a longitudinal direction along left and right sides of the liquid permeable top layer, wherein the absorbent core at least comprises a rear hip section and a crotch section, the absorbent core having a front-side film extended to form a front lifting section, the absorbent article having a rear waist side film extended to form a rear lifting film, wherein the rear lifting film is provided, in left and right sides, with at least one aperture that allows male and female parts of a hook-and-loop fastener to engage for fastening and lifting and the front lifting section is provided, in left and right sides, with at least one aperture that allows male and female parts of a hook-and-loop fastener to engage for fastening and lifting.

The absorbent core comprises the rear hip section and the crotch section, wherein the absorbent core has a front end that is formed with two projecting portions adapted to respectively extend on left and right sides of an external sex organ of a male wearer, and a recessed portion that is formed between the two projecting portions and is provided, at a location corresponding to a root portion of a scrotum of the wearer, with an easy tear line that selectively defines an opening extending in a direction toward a belly of the wearer to form an isolating absorbent article, thereby allowing tightly surrounding around the rear root portion of the scrotum after selective tearing in order to isolate the external sex organ.

The absorbent article, wherein the easy tear line opening is in the form of a longitudinal straight line; or the easy tear line opening is in the form of a V-shaped line having an internal angle smaller than 20°; or the easy tear line opening is of a capsule shape or an elliptic shape and having a top end connected with a longitudinal straight line, the capsule shape or the elliptic shape having a transverse minor axis having a length less than 1 cm and a the longitudinal major axis having a length of 2.5-8 cm; or the easy tear line opening is in the form of an inverted A-shaped line; or the easy tear line opening is in the form of multiple straight lines intersecting at a center point and including an upward-extending longitudinal straight line, the straight lines being tearable apart and foldable to form an elliptic shape of the opening, wherein the elliptic shape has a transverse minor axis having a length of 1.5-3 cm and a longitudinal major axis having a length of 6 cm±2 cm.

The absorbent core is structured such that the absorbent core further comprises a front belly section extending from a front end of the crotch section to a height that is adapted to correspond to one half of a belly of a wearer±2 cm, wherein the front belly section comprises a film that is provided with an easy tear line that selectively defining an opening extending along an outer circumference of the front belly section of the absorbent core to form a shielding absorbent article.

A second objective of the present invention is an isolating absorbent article (2) having a nonwoven-fabric (nonwoven textile structure) surface layer, which is attached to and engaging with a hook-and-loop fastener male part provided on an inside surface of a rear pad of enclosing pants the rear pad the for fixing so as to eliminate the need for forming apertures thereby saving mounting material and easing wearing.

To achieve the above objective, a technical solution adopted in this invention is an absorbent article, which comprises a liquid permeable top layer, a liquid impermeable bottom layer, an absorbent core disposed between the liquid permeable top layer and the liquid impermeable bottom layer, and a leaking protection barrier extending in a longitudinal direction along left and right sides of the liquid permeable top layer, wherein the absorbent core comprises a rear hip section and a crotch section, the absorbent core having a front-side film extended to form a front lifting section, wherein the absorbent core has a front end that is formed with two projecting portions adapted to respectively extend on left and right sides of an external sex organ of a male wearer, and a recessed portion that is formed between the two projecting portions and is provided, at a location corresponding to a root portion of a scrotum of the wearer, with an easy tear line that selectively defines an opening extending in a direction toward a belly of the wearer to form an isolating absorbent article, thereby allowing tightly surrounding around the rear root portion of the scrotum after selective tearing in order to isolate the external sex organ.

The absorbent article, wherein the bottom layer is combined with a nonwoven-fabric surface layer of fibers or a high-loft material.

The absorbent article, wherein the bottom layer has a back surface that is provided with adhesive for fixing to an inside surface of a rear pad of the enclosing pants.

The absorbent article, wherein the easy tear line opening is in the form of a longitudinal straight line; or the easy tear line opening is in the form of a V-shaped line having an internal angle smaller than 20°; or the easy tear line opening is of a capsule shape or an elliptic shape and having a top end connected with a longitudinal straight line, the capsule shape or the elliptic shape having a transverse minor axis having a length less than 1 cm and a the longitudinal major axis having a length of 2.5-8 cm; or the easy tear line opening is in the form of an inverted A-shaped line; or the easy tear line opening is in the form of multiple straight lines intersecting at a center point and including an upward-extending longitudinal straight line, the straight lines being tearable apart and foldable to form an elliptic shape of the opening, wherein the elliptic shape has a transverse minor axis having a length of 1.5-3 cm and a longitudinal major axis having a length of 6 cm±2 cm.

A third objective of the present invention is to provide enclosing pants, which is wearable in combination with an absorbent article. The enclosing pants has a rear pad having two lifting and looping sections and a central opening section, and an aperture for fixing the absorbent article, and allowing an external sex organ to expose outside the rear pad or for looping up left and right sides of a front belly section of a shielding absorbent article (for reducing width of an absorbent core layer and also preventing side leaking of urine), wherein after a front pad and the rear pad are positioned and fastened (without being detached after being positioned and fastened), so that it only needs to fasten the other side without the concern of incorrect wearing, and being capable of opening and closing for fixing a urine tube and replacing and fixing a urine sack, and adjusting a spacing distance of fastening for left and right sides (to prevent compression of the urine sack that causes reversal flow or overflowing of urine), front and the rear fastening units being fastened in a direction from outside to inside (to expand application of sizes of absorbent article), or an inside surface of the rear pad being provided with a hook-and-loop fastener male part for engaging and attaching to the nonwoven-fabric surface layer of the absorbent article (to save a length of a base material for more than 10 cm, easing installation, and allowing for easy positioning of a urine tube between male and female parts that are in engagement with each other for retaining), wherein replacing diapers six times a day may be reduced to replacing the absorbent article for just one time with the use of the urine sack, so as to provide a great effect for environment protection.

To achieve the above objective, a technical solution adopted in this invention comprises enclosing pants comprising a rear pad, which comprises a rear waist section, a rear hip section, a crotch section extending from a lower end of the rear hip section, elastic extension/contraction sections arranged on the rear waist section at locations adjacent to left and right sides, respectively, rear wing sections connected to the left and right sides of the rear waist section respectively and each having an extension section, two lifting and looping sections respectively arranged leftward and rightward and connected to a front end of the crotch section for respectively corresponding to the extension sections, a central opening section defined by the two lifting and looping sections collectively, and thigh circumference extension/contraction edges respectively arranged at edges of left and right sides of the rear hip section and the crotch section; and a front pad, which comprises a front waist section, a front belly section, a down-extension section that is adapted to cover a male external sex organ, and front wing sections arranged at left and right sides of the front waist section and respectively corresponding to the rear wing sections; wherein the extension sections and the lifting and looping sections are engageable with and attached to each other by means of a first fastener, in a detachable manner, on left and right belly portions of the wearer; the rear wing sections and the front wing sections are engageable with and attached to each other by means of second fasteners, in a detachable manner; and the lifting and looping sections and the front pad are engageable with and attached to each other by means of third fasteners, in a detachable manner, on the left and right belly portions of the wearer.

The enclosing pants further comprises one positioning fastener group, which comprises buttons that are provided on an outside surface of one of the rear wing sections and arranged to line up in a top-bottom direction and slits formed in a corresponding one of the front wing sections and arranged to line up in a left-right direction, or comprising a hook arranged on an inside surface of one of the front wing plate and multiple ring rows arranged on an outside surface of a corresponding one of the rear wing plates and lining up in a top-bottom direction, the ring rows comprising multiple rings arranged to line up in a left-right direction, or comprising ring buckles arranged on an outside surface of one of the rear wing plates and lining up in a top-bottom direction and a buckle strap arranged on an inside surface of a corresponding one of the front wing plates.

The enclosing pants further comprises two positioning fastener groups, each of which comprises a button arranged on an end of an outside surface of each of the lifting and looping sections and slits formed in a corresponding location of the front pad and arranged to line up in a top-bottom direction.

The enclosing pants are structured such that the lifting and looping section of one of the two sides or of each of the two sides has an upper end that is fixed, through sewing or riveting, to a corresponding surface of the front pad.

The enclosing pants are structured such that an inside surface of the rear hip section and the lifting and looping sections is provided with a hook-and-loop fastener male part to receive a nonwoven-fabric surface layer of the absorbent article to attach thereto and engage therewith.

The enclosing pants further comprising a front fastening unit and a rear fastening unit that are arranged opposite to each other on that front waist section and that rear waist section the front fastening unit and the rear fastening unit that are foldable from an outside surface onto an inside surface for fastening and each comprising two hook-and-loop fastener male parts symmetrically arranged on the outside surface and foldable from outside toward inside for fastening and two hook-and-loop fastener female parts associated therewith are respectively set on and cover, in a corresponding manner, the inside surface and the outside surface; and a connection portion arranged on the outside surface in a horizontal direction at a location below the hook-and-loop fastener female parts, wherein the connection portion is provided, on left and right end parts of an inside surface thereof, with the hook-and-loop fastener male parts respectively.

The enclosing pants, wherein the connection portion further a recessed portion being provided between the two male parts adapted to avoid contacting and staining by fecal matter.

The enclosing pants are structured such that the crotch section has a front end extended to a position adapted to correspond to a body surface of a wearer at an upper end of the pubic bone to form an upward-extending section, and an outside surface is provided with a separation portion of the third fastener female part.

A fourth objective of the present invention is to provide a method for wearing a combination of the aperture-included isolating absorbent article (1) and the enclosing pants.

A fifth objective of the present invention is to provide a method for wearing a combination of the aperture-included shielding absorbent article (3) and the enclosing pants.

A sixth objective of the present invention is to provide a method for wearing a combination of the nonwoven-fabric-surface-layer-included isolating absorbent article (2) and the enclosing pants.

BRIEF DESCRIPTION OF THE DRAWINGS

FIG. 1Aa is a schematic perspective-view showing the example of FIG. 1A in an enlarged form (the easy tear line being torn apart).

FIG. 2Aa is a schematic perspective view showing the example of FIG. 2A in an enlarged form (the easy tear line being torn apart).

FIG. 3Aa is a schematic perspective view showing the example of FIG. 3A in an enlarged form (the easy tear line being torn apart).

DETAILED DESCRIPTION OF THE PREFERRED EMBODIMENT

Figure 14A:
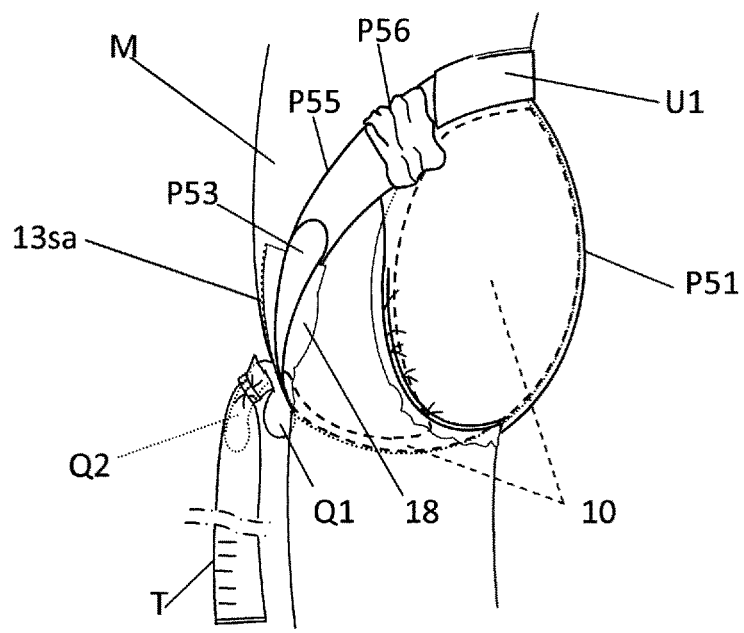
FIGS. 14A and 14B, which are provided for comparison, are schematic views respectively showing, after being installed with a urine sack, conditions anterior to (in a side view) and posterior to (in a front view) covering of a front pad.
Figure 14B:
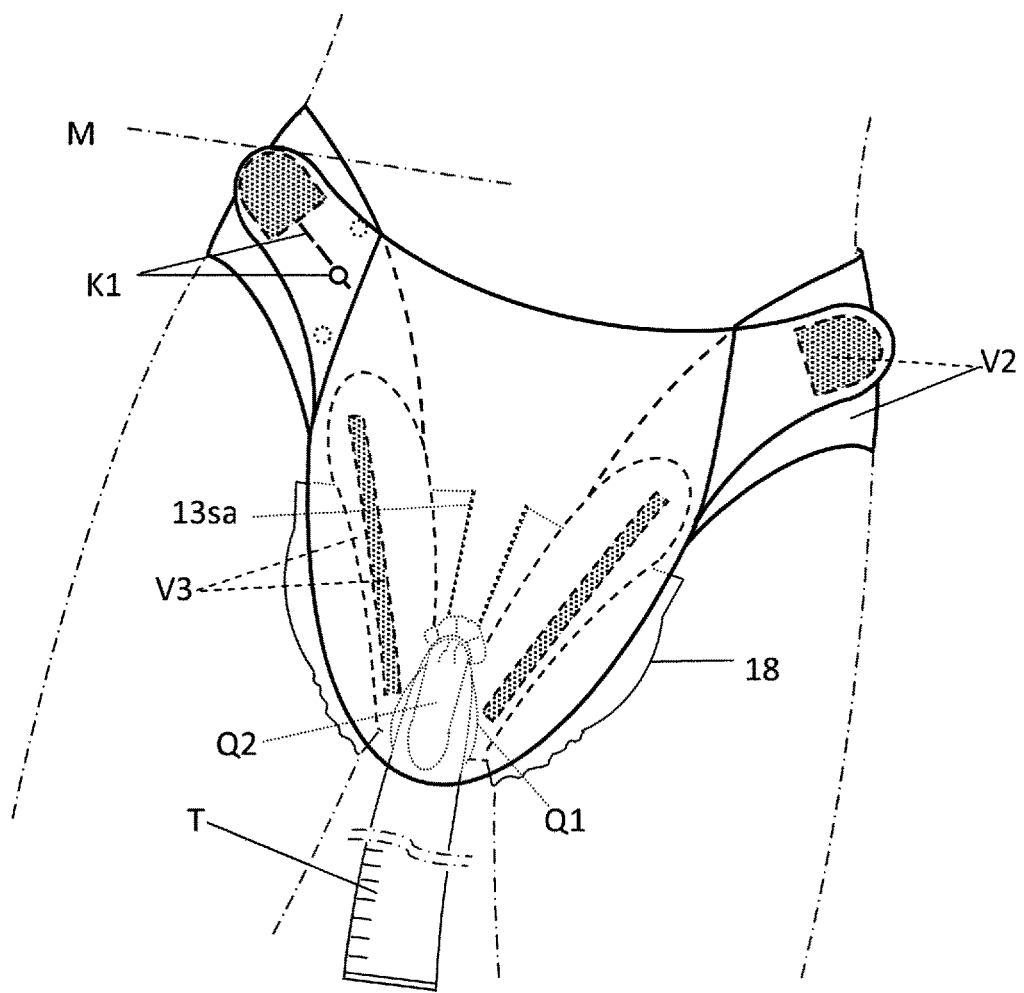

The following provides a description that is made by taking a front standing posture of a wearer as an example for explanation of directions, positions, and sizes of technical solutions provided in the present invention. The term "urine sack" as used herein refers to a simply-structured elongate flexible bag that can be fit over a penis (examples of which include the part designated at T in FIGS. 14A and 14B and those disclosed in Taiwan Utility Model TWM265025); the term "hook-and-loop fastener male part" as used herein refers to a hooked pad, and "female part" is a looped pad; the term "nonwoven fabric" as used herein refers to a material that is formed as being bonded through a manner that is not weaving and knitting; the term "composite film" as used herein refers to a structure including an impermeable internal film bonded to a nonwoven-fabric surface layer combined with fibers or a high-loft material.

Figure 3A:
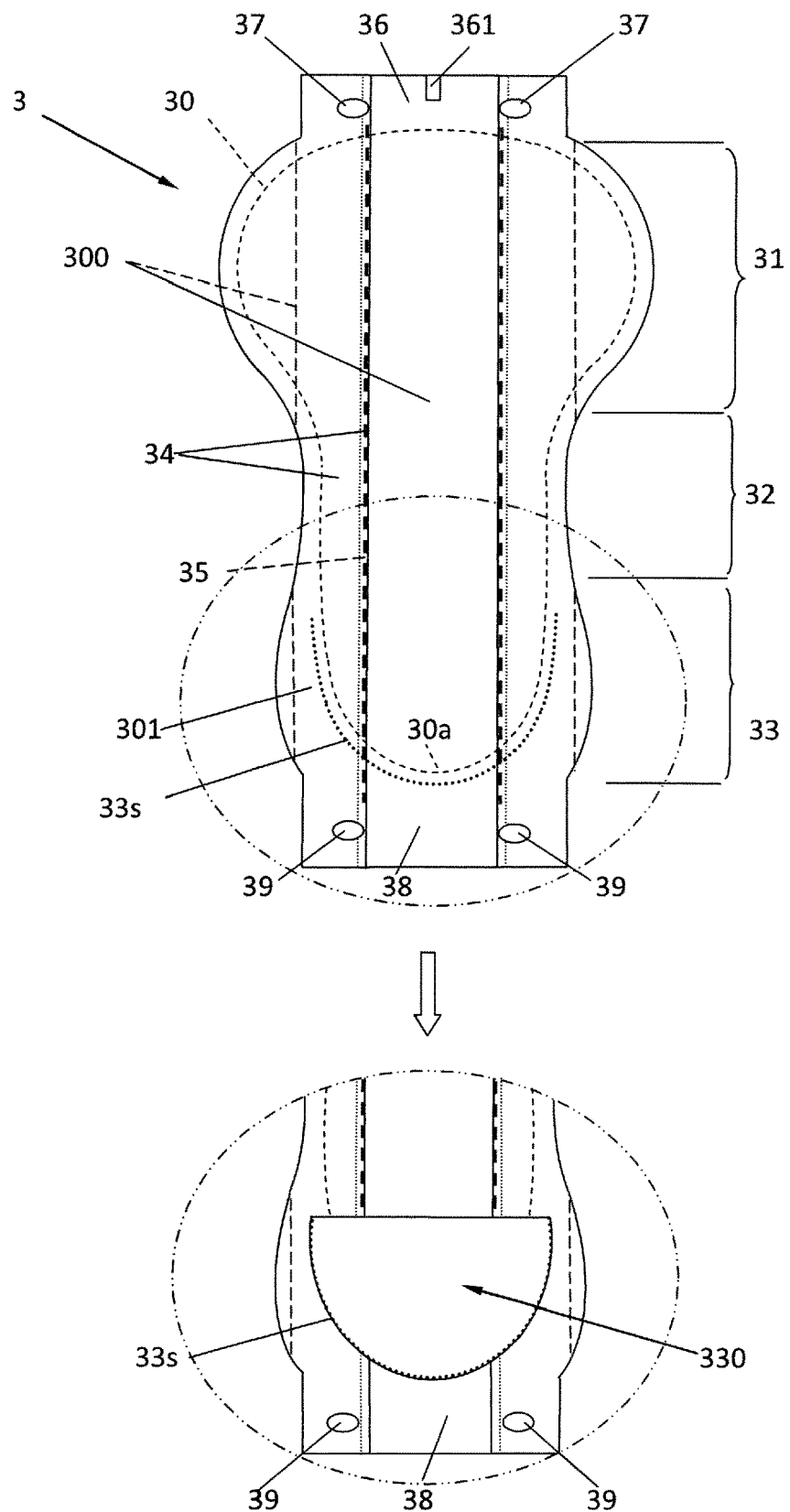
FIG. 3A is a schematic top plan view showing an example of an aperture-included shielding absorbent article in a developed form, including an easy tear line opening formed of a longitudinal straight line, and also showing, in proportion, the easy tear line opening in a torn-apart condition.
Figure 3A:
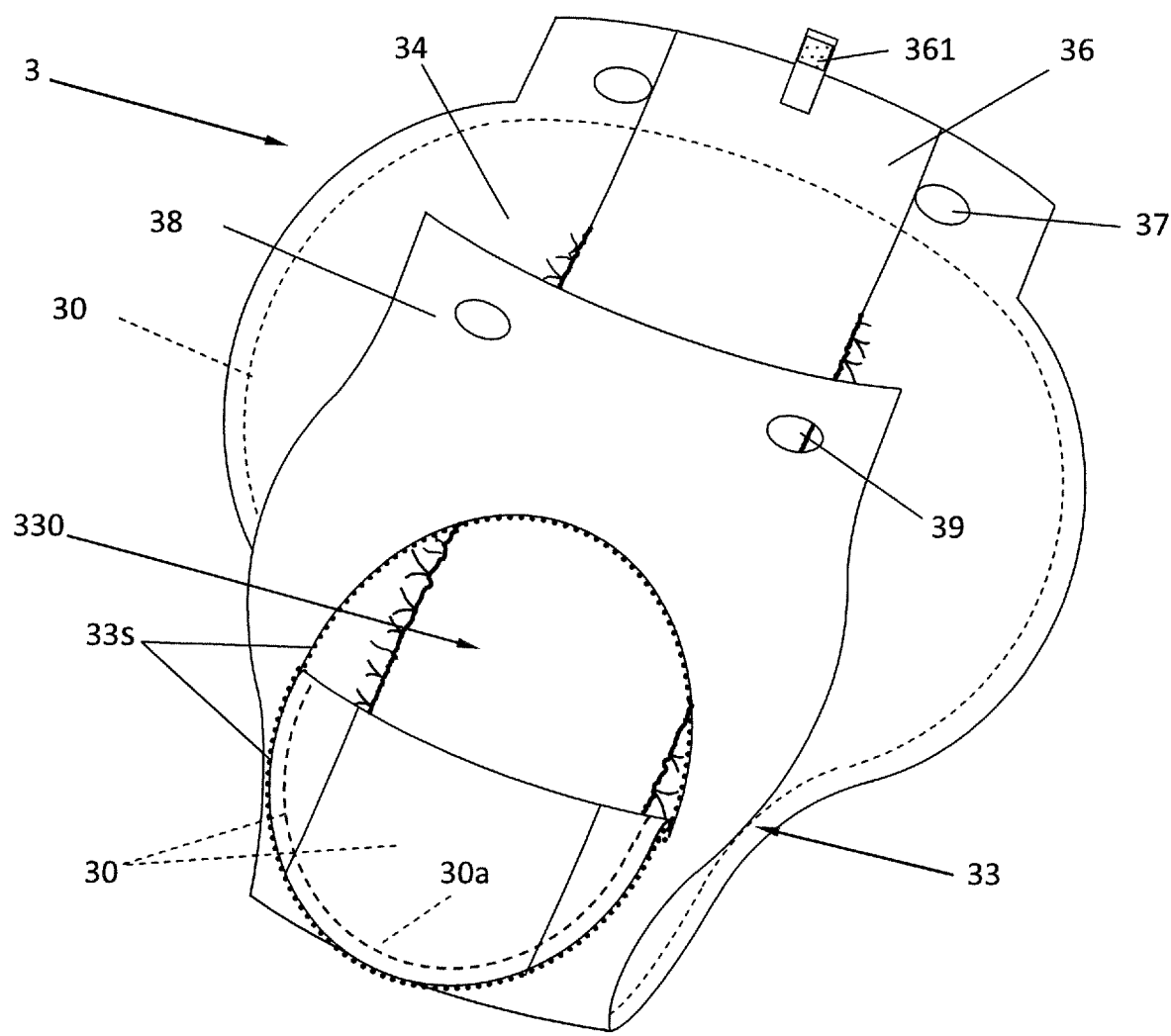

FIGS. 1A-1E illustrate an aperture-included isolating absorbent article, generally designated at 1, according to the present invention; FIGS. 2A-2E illustrate a nonwoven-fabric-surface-layer-included isolating absorbent article, generally designated at 2, according to the present invention; and FIGS. 3A and 3Aa illustrate an aperture-included shielding absorbent article, generally designated at 3, according to the present invention, and these absorbent articles comprise: a liquid permeable top layer 100, 200, 300, a liquid impermeable bottom layer, an absorbent core 10, 20, 30 disposed between the liquid permeable top layer and the liquid impermeable bottom layer, and a leaking protection barrier 14, 24, 34 that is arranged to extend, in a longitudinal direction, along left and right sides of the liquid permeable top layer (as being publicly known as a barrier that is formed by having two hydrophobic films each opposite edges wrapped around an elastic element 15, 25, 35 so as to contract to provide a three-dimensional configuration when worn).

In the absorbent article 1, 3, the absorbent core has a front-side film that is extended to form a front lifting section 18, 38 and a rear waist side film that is extended to form a rear lifting film 16, 36. The rear lifting film is provided, on left and right sides, with at least one aperture 17, 37 that allows male and female parts of a hook-and-loop fastener to engage for fastening and lifting. The front lifting section is provided, on the left and right sides, with at least one aperture 19, 39 that allows male and female parts of a hook-and-loop fastener to engage for fastening and lifting.

Figure 1A:
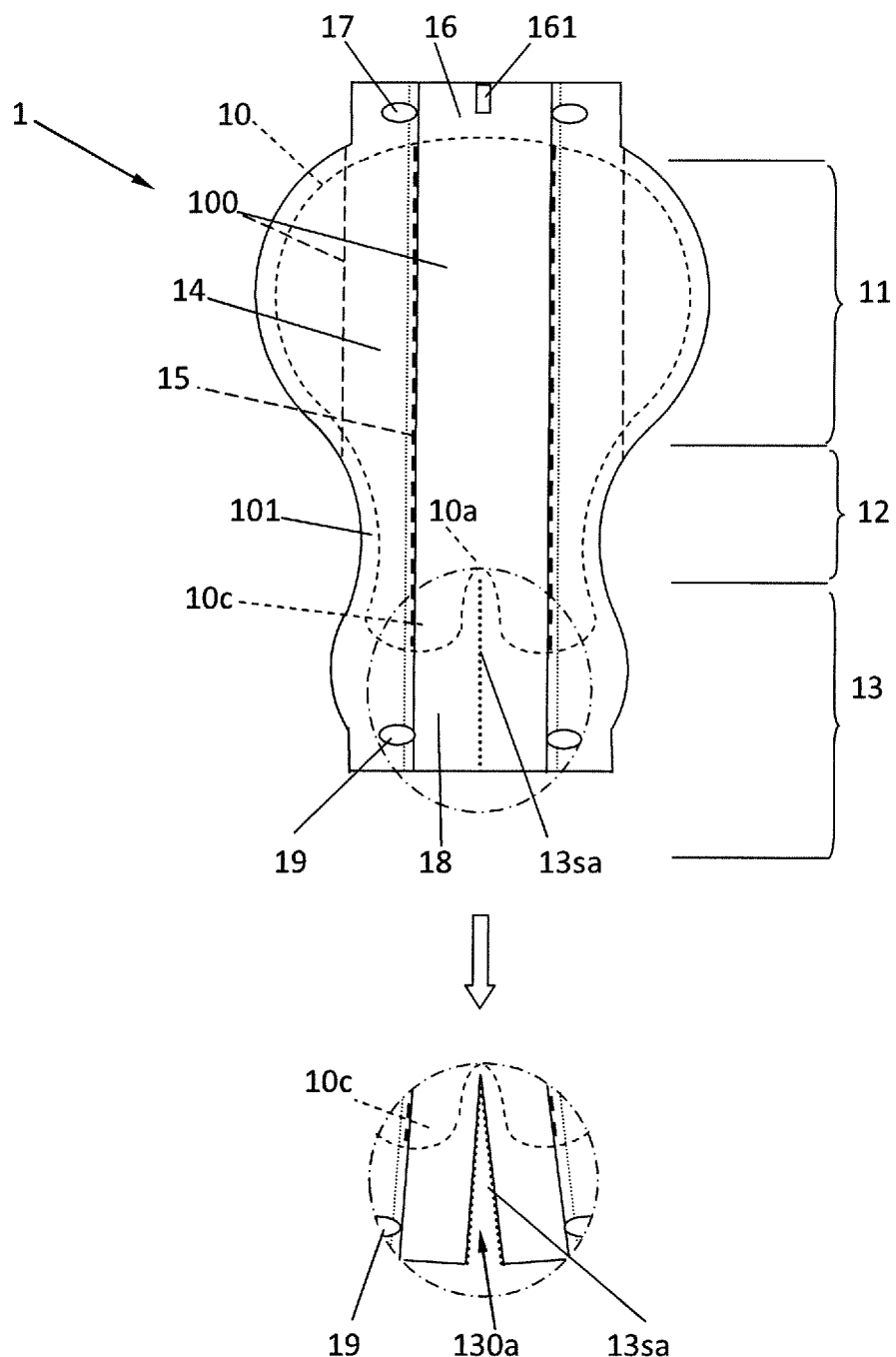
FIG. 1A is a schematic top plan view showing an example of an aperture-included isolating absorbent article in a developed form, including an easy tear line opening formed of a longitudinal straight line, and also showing, in proportion, the easy tear line opening in a torn-apart condition.
Figure 1A:
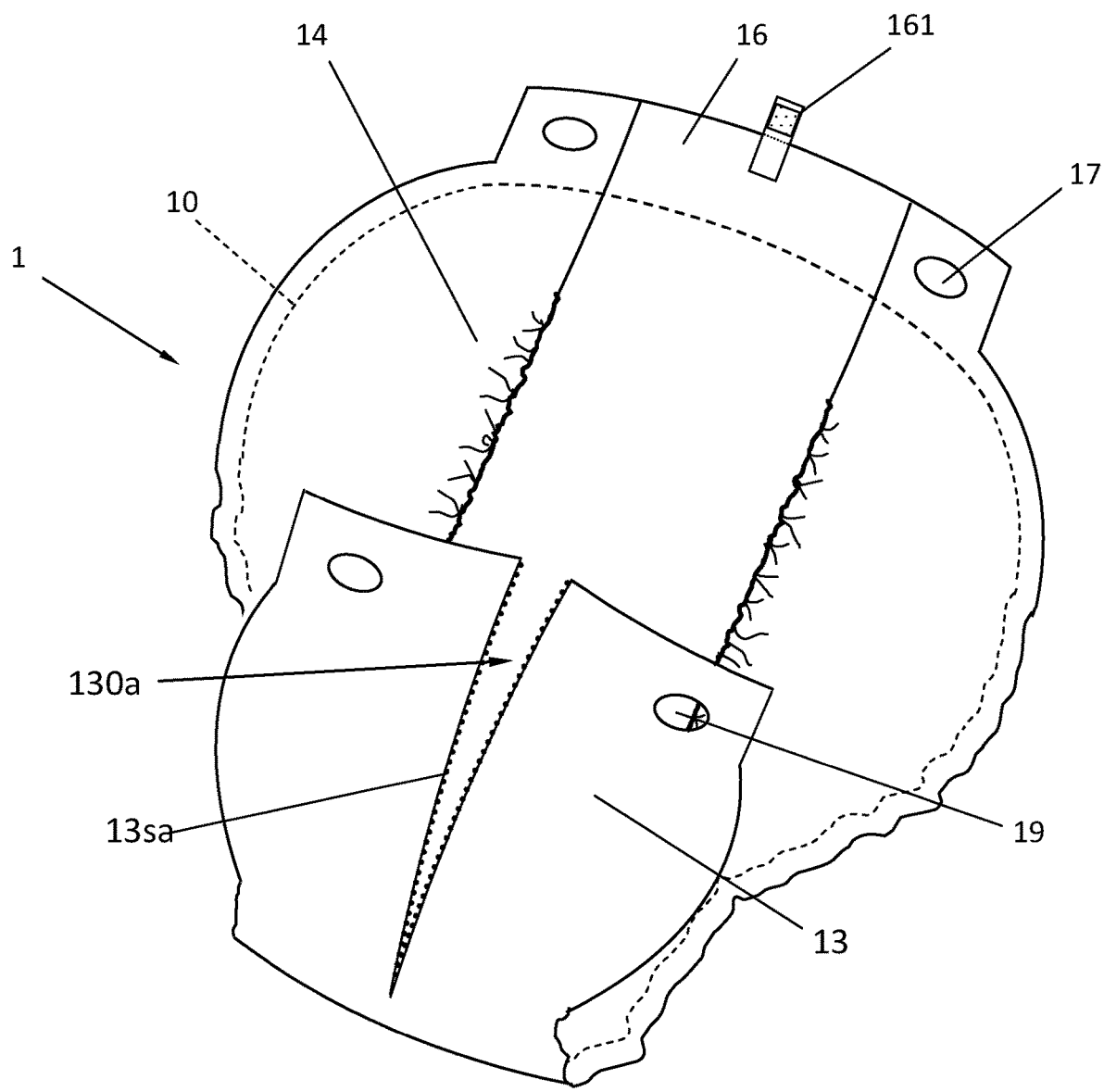
Figure 1B:
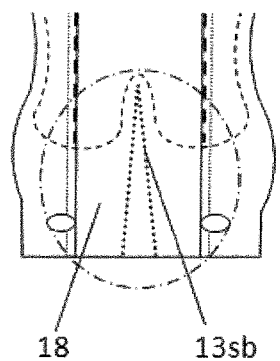
FIGS. 1B-1E are schematic top plan views showing, in a developed faun, examples of different configurations of an absorbent article of FIG. 1A that include an easy tear line opening a V-shaped line (FIG. 1B), a capsule or elliptical shape having an end connected with a longitudinal straight line (FIG. 1C), an inverted A-shaped line (FIG. 1D), multiple straight lines intersecting at a center and including an upward-extending longitudinal straight line (FIG. 1E), and also showing, in proportion, the easy tear line openings in a torn-apart condition.
Figure 1B:
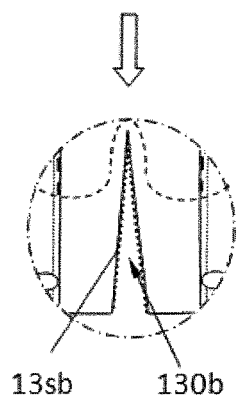
Figure 1C:
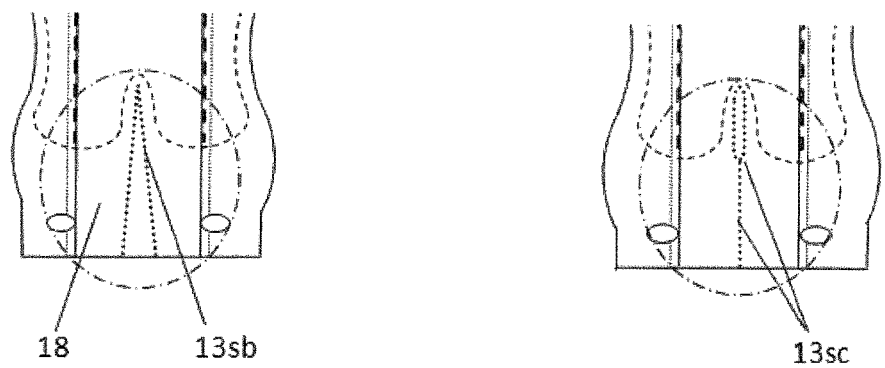
Figure 1C:
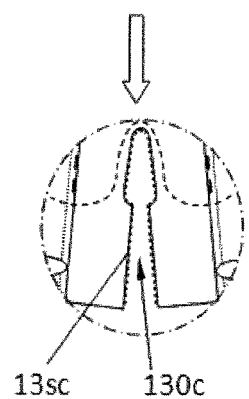
Figure 1D:
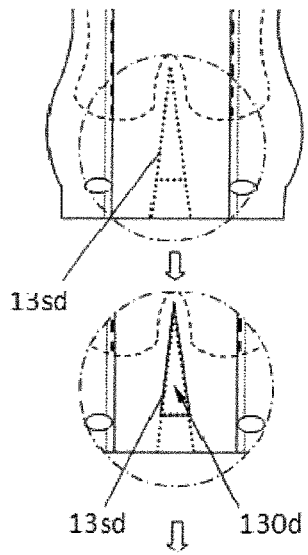
Figure 1D:
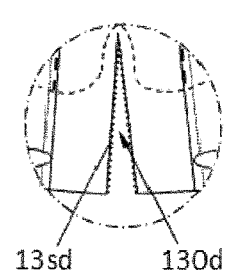
Figure 1E:
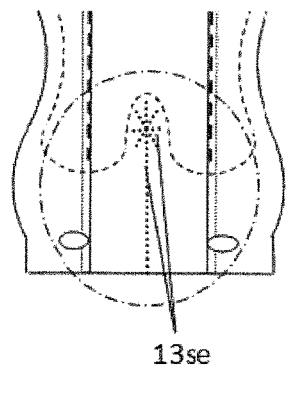
Figure 1E:
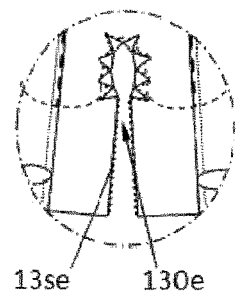
Figure 2A:
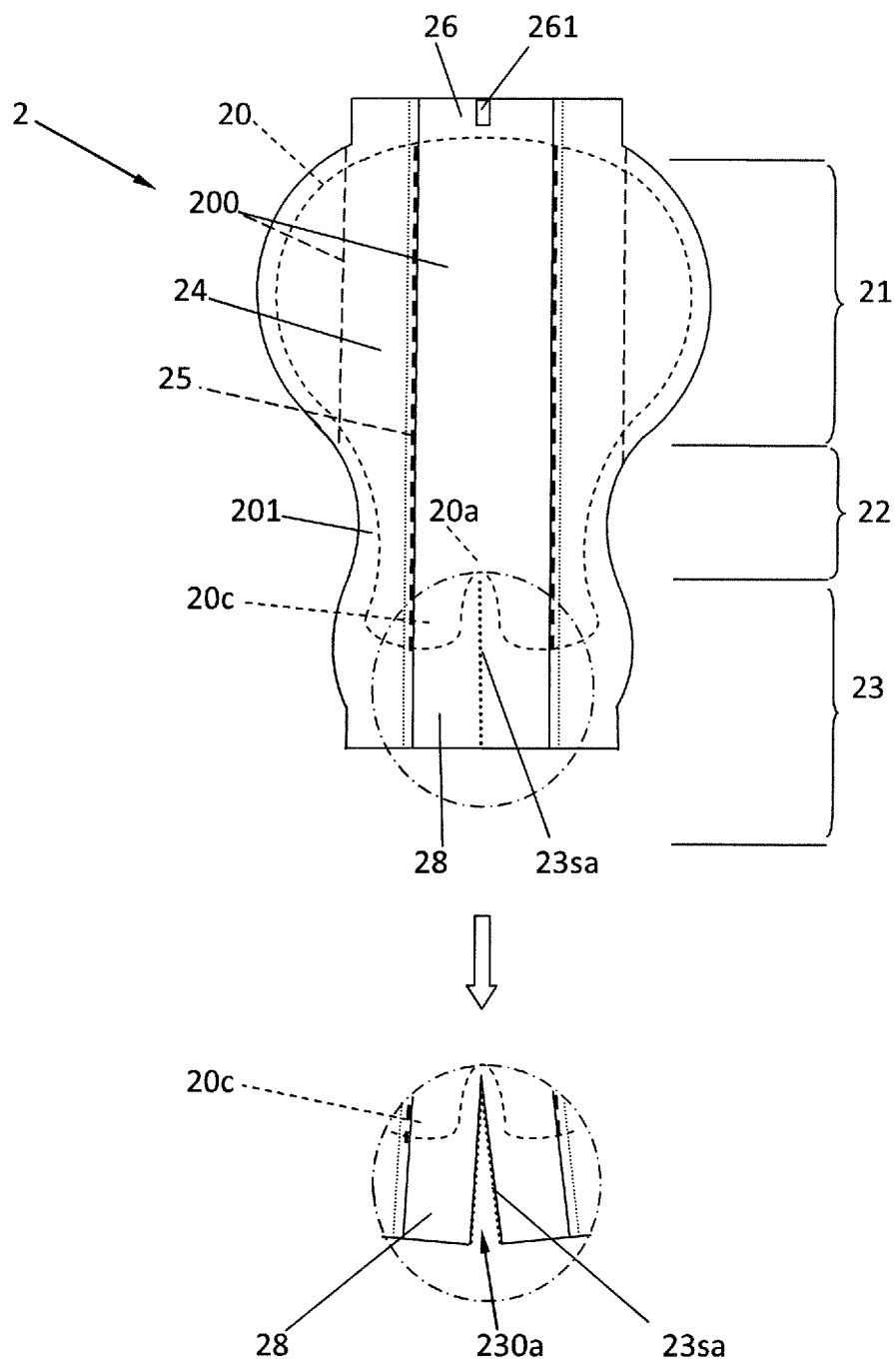
FIG. 2A is a schematic perspective view showing a nonwoven-fabric-surface-layer-included isolating absorbent article, including an easy tear line opening formed of a longitudinal straight line, and also showing, in proportion, the easy tear line opening in a torn-apart condition.
Figure 2A:
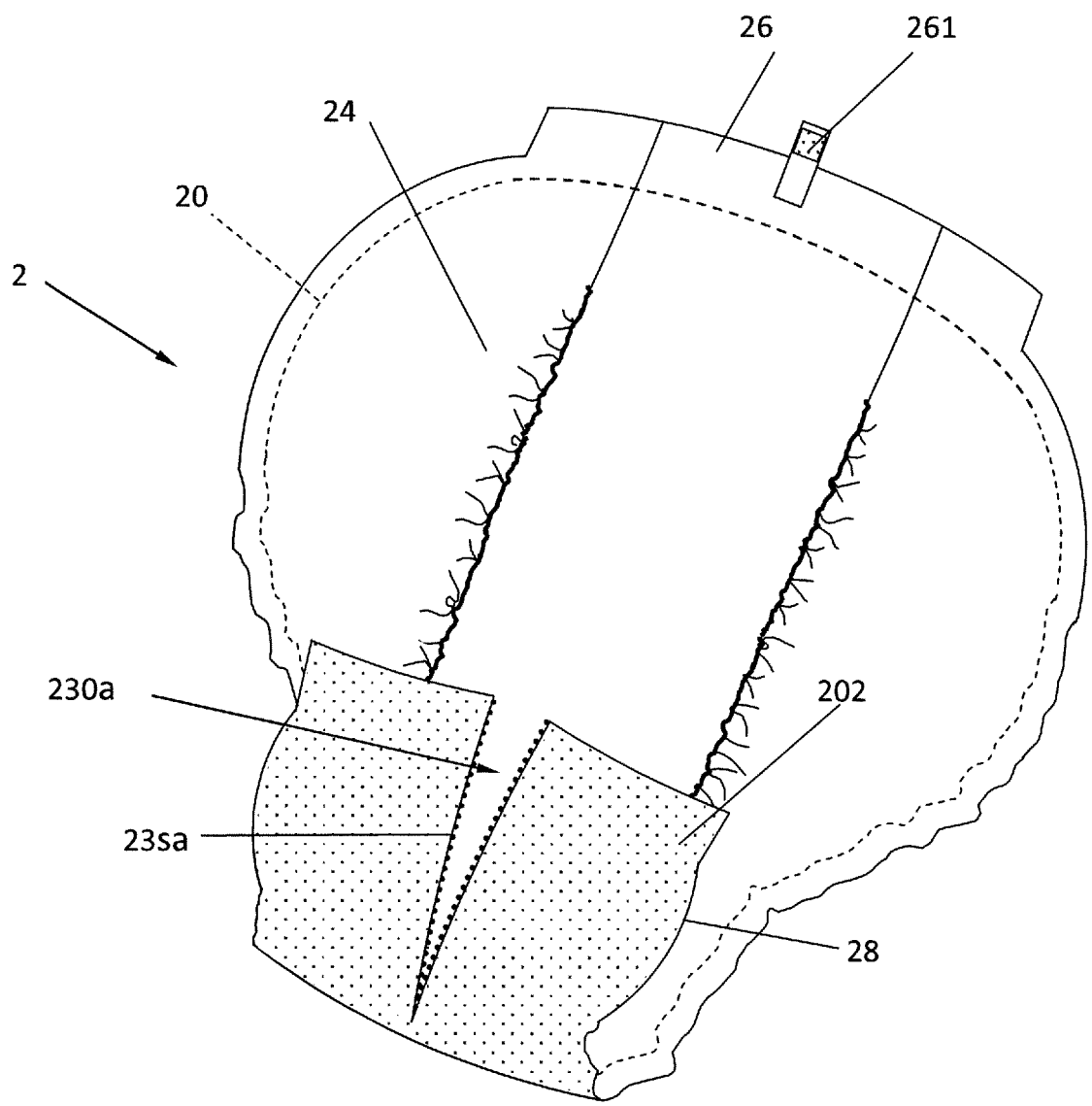
Figure 2B:
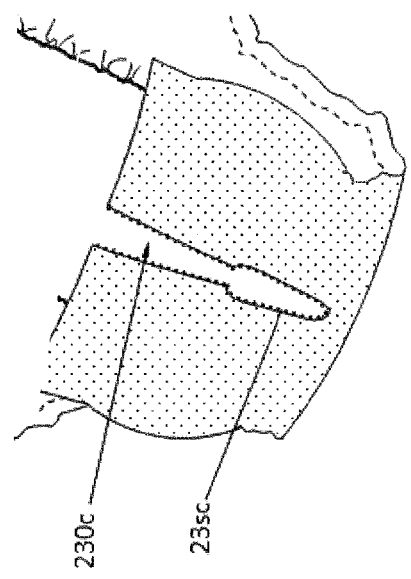
FIGS. 2B-2E are examples of different configurations of the absorbent article of FIG. 2A, which, as shown in a torn-apart condition, include an easy tear line opening in the form of a longitudinal straight line (FIG. 2A), a V-shaped line (FIG. 2B), a generally capsule or elliptical shape having an end connected with a longitudinal straight line (FIG. 2C), an inverted A-shaped line (FIG. 2D), multiple straight lines intersecting at a center and including an upward-extending longitudinal straight line (FIG. 2E).
Figure 2C:
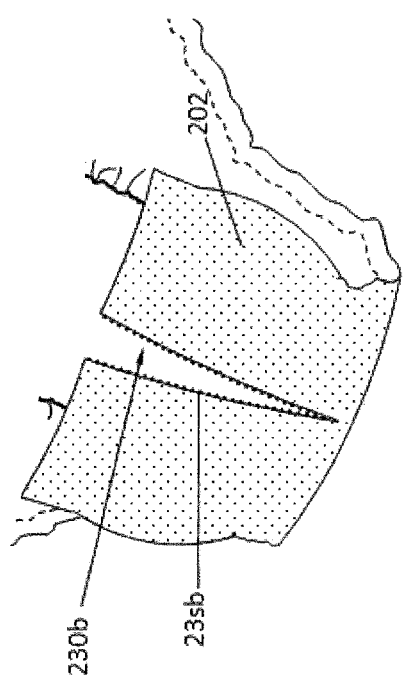
Figure 2D:
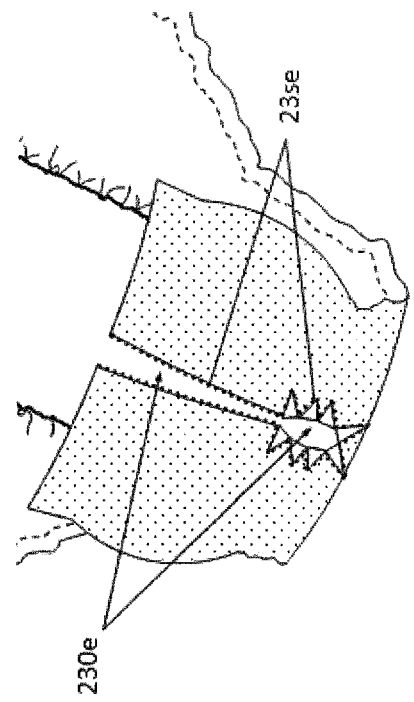
Figure 2E:
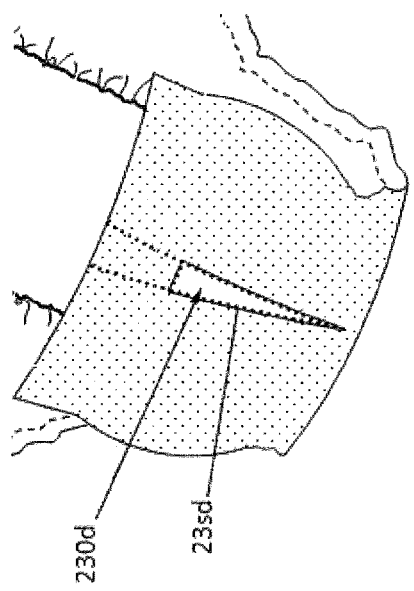
Figure 7:
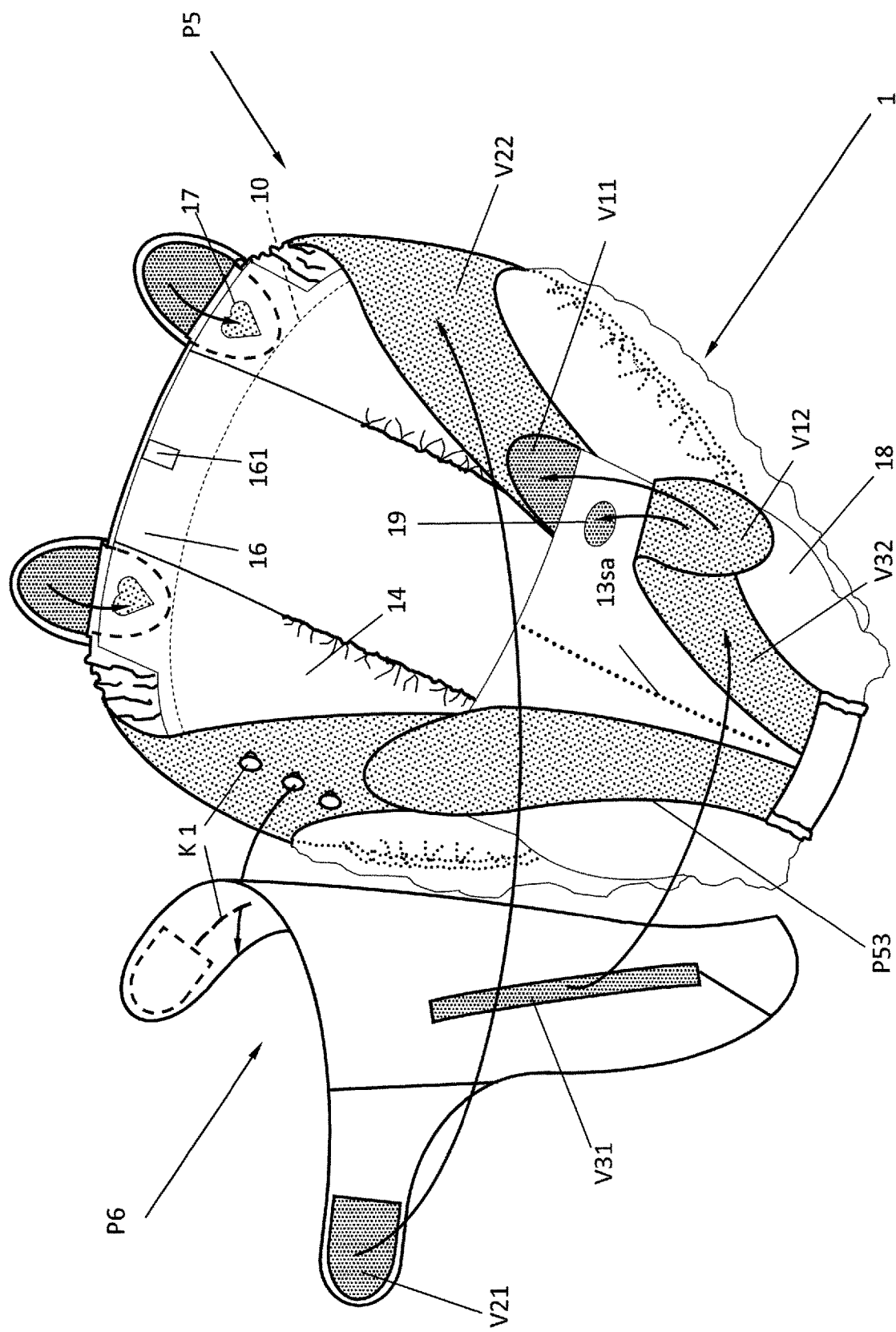
FIG. 7 is a schematic perspective view showing the enclosing pants being disposed with the aperture-included isolating absorbent article.
Figure 10:
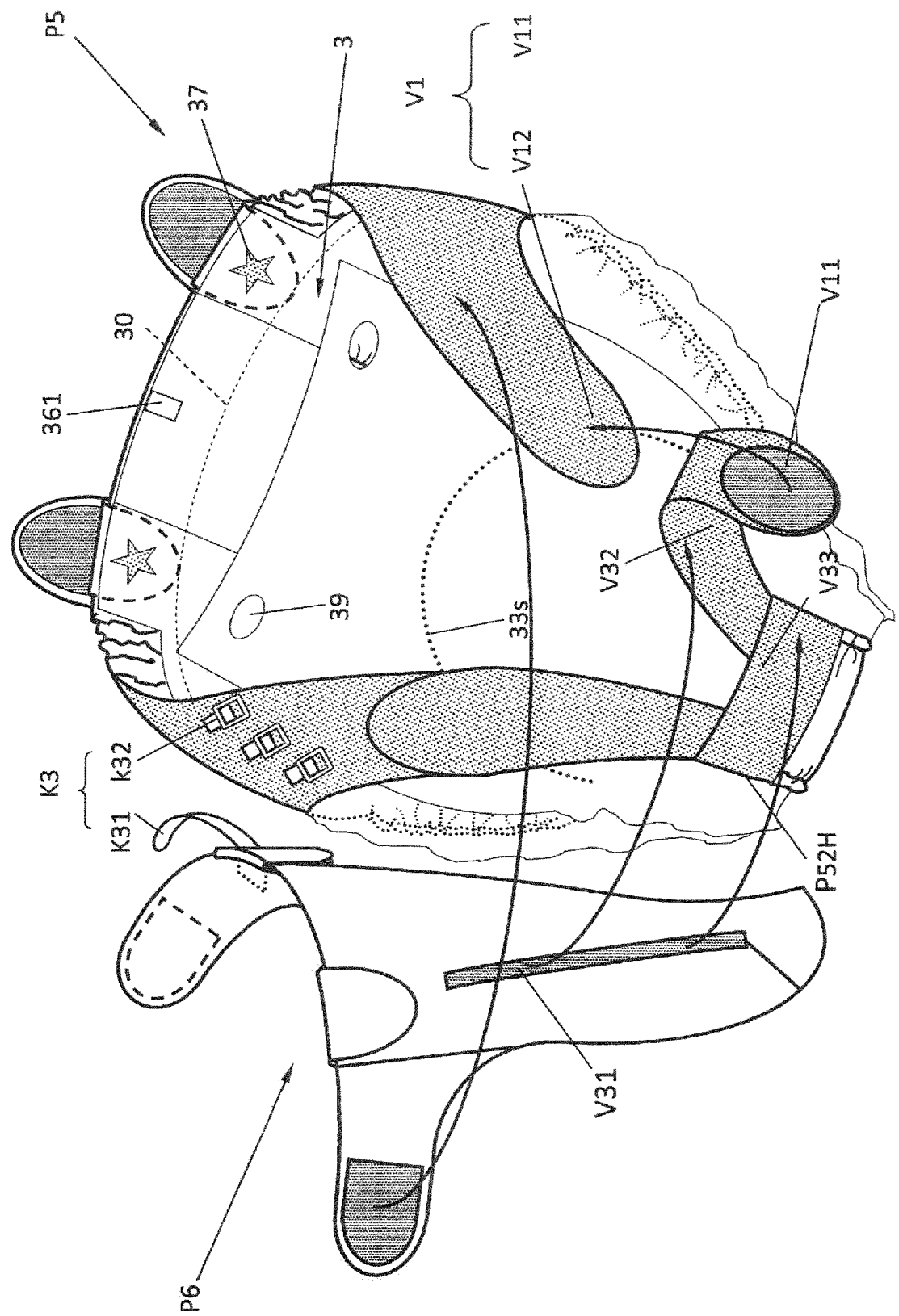
FIG. 10 is a schematic perspective view showing the enclosing pants being disposed with the shielding absorbent article.

The apertures as mentioned above are exemplified with an elliptic shape as shown in FIG. 1A, of which, preferably, a short diameter is for example 2-3 cm and a long diameter is for example 2.5-3.5 cm; or alternatively, they can be replaced with multiple holes having smaller diameters. Examples of the aperture can be one having a planar configuration in the form of a heart shape (such as holes 17 of FIG. 7), a star shape (such as holes 37 of FIG. 10), and those of any geometric shapes (provided for easy direction recognition or classification).

In another embodiment, an absorbent article is simply provided with only the aperture, in which the absorbent core may at least comprise a rear hip section and a crotch section and is still wearable by using enclosing pants.

In the absorbent article 3, the absorbent core 30 comprises a rear hip section 31 and a crotch section 32, and a front belly section 33 extending from a front end of the crotch section to a height that is one half of a wearer's belly±2 cm, wherein the front belly section comprises a film 301 that is provided with an easy tear line 33s extending along an outer circumference of the front belly section of the absorbent core as an opening 330 to form a shielding absorbent article, which is selectively torn open and folded downward to allow a male wearer to install a urine sack or simply for ventilation.

In the absorbent article 1, 2, the absorbent core comprises a rear hip section 11, 21 and a crotch section 12, 22, and a front part of the crotch section is a front lifting section. The absorbent core front end 10a, 20a has two projecting portions 10c, 20c respectively extending on left and right sides of the external sex organ of a male wearer and a recessed portion formed between the two projecting portions corresponds, in position, to a root of the scrotum and is provided with an easy tear line opening that is open in a direction toward the belly, which allows, after selective tearing, for closely surrounding the rear root portion of the scrotum for isolating the external sex organ.

In another embodiment, an absorbent article that is only provided with the two projecting portions and the easy tear line opening may be applied by using enclosing pants that is provided with snap touch fasteners that correspond to each other to fasten and clamp the film (not shown) of the rear waist section and the front lifting section.

Figure 8:
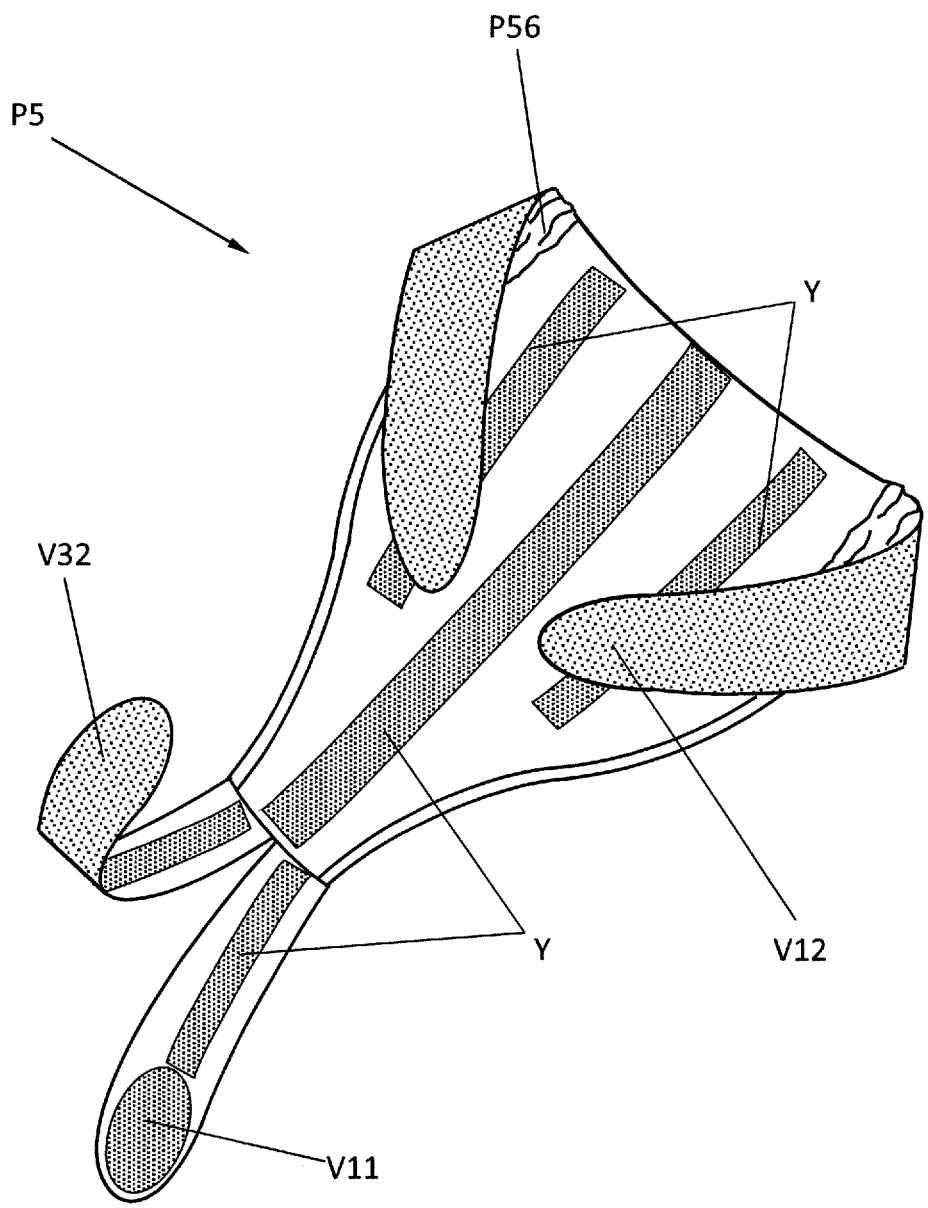
FIG. 8 is a schematic view showing the enclosing pants being disposed with a hook-and-loop fastener male part on an inside surface of the rear pad.
Figure 13A:
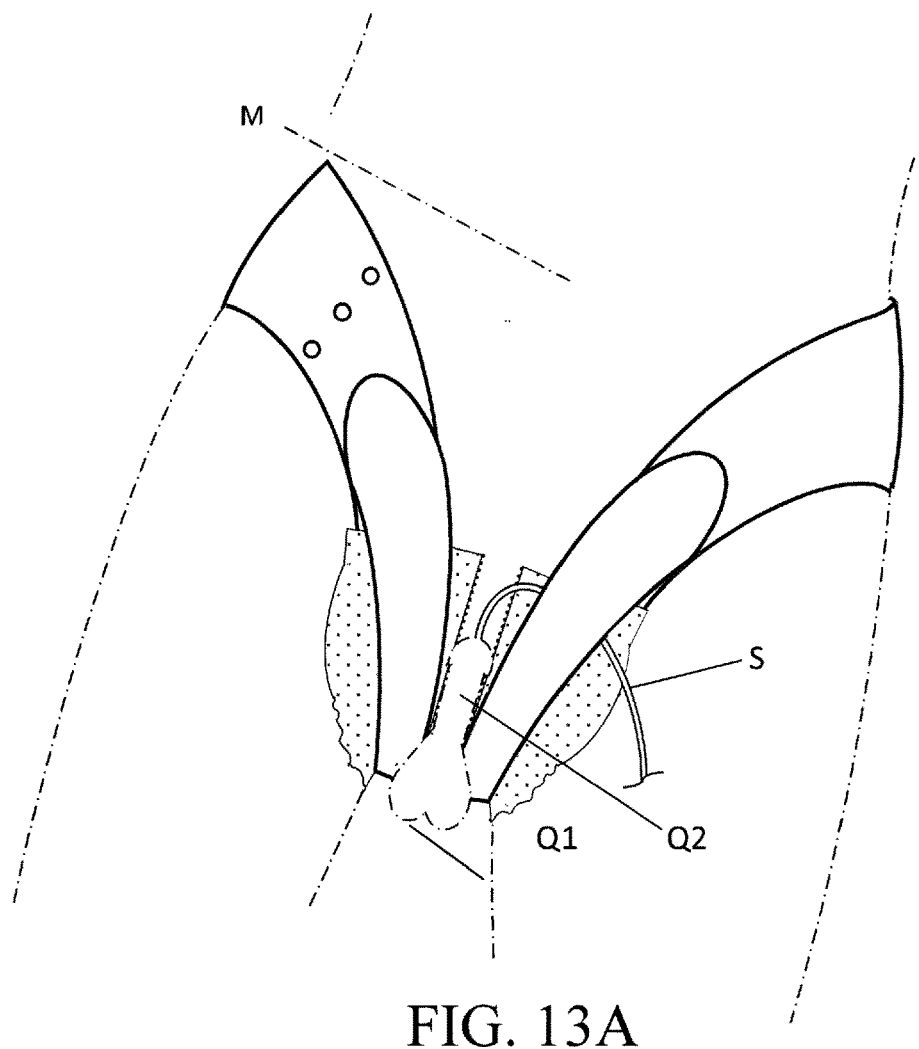
FIGS. 13A and 13B, which are provided for comparison, are schematic views respectively showing a male and a female wearing the nonwoven-fabric-surface-layer isolating absorbent article, where a urine tube is retained at a position between a lifting and looping section and a nonwoven-fabric surface layer.
Figure 13B:
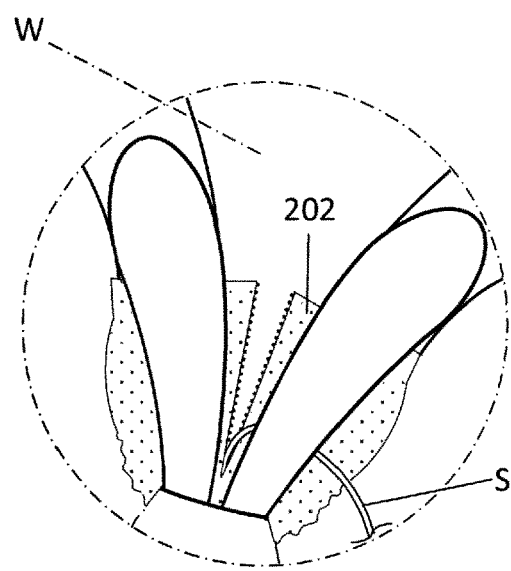

In other embodiments, the rear lifting film 26 and the front lifting section 28 of the absorbent article 2 are not formed with apertures, wherein the bottom layer comprises and is combined with a nonwoven-fabric surface layer 202 of fibers or a high-loft material (the term "combined" as used herein referring to for example formation of a composite film that publicly known) for attaching engagement with a hook-and-loop fastener male part Y (FIG. 8) provided on an inside surface of the enclosing pants for easy retention of an urine tube S between the male and female parts so attached to and engaging with each other (FIGS. 13A and 13B).

In a further embodiment, the bottom layer is provided, on a back surface thereof, with adhesive for fixing to the inside surface of the enclosing pants.

As shown in FIGS. 1B-1E and 2B-2E, in the absorbent article 1, 2, the easy tear line may define an opening 130a, 230a formed of a longitudinal straight line 13sa, 23sa, or an opening 130b, 230b having an internal angel smaller than 20° formed of a V-shaped line 13sb, 23sb, or an opening 130c, 230c generally capsule form or an elliptic form having an end connected with a longitudinal straight line 13sc, 23sc, or an opening 130d, 230d formed of an inverted A-shaped line 13sd, 23sd, or an opening 130e, 230e formed of multiple straight lines intersecting at a center and including an upward-extending longitudinal straight line, such intersecting straight lines 130se, 230se being applicable to form an elliptic opening after being torn apart and folded, the length of the transverse minor axis of the elliptic shape being 1.5-3 cm, the length of the longitudinal major axis being 6 cm±2 cm.

In such arrangements, the opening formed of the inverted A-shaped line only allows tearing a lower side inverted triangular part, to allow a device, such as a penis sheath in the form of a condom or a urine stopping sack (such as the disclosures of Taiwan Utility Models TWM483072 and TWM341501) to penetrate out once together with the external sex organ for pulling and lifting and fast mounting of hook-and-loop engagement, and also for re-tearing of the upper side inverted trapezoid in replacing the absorbent article, or for one time or entirely tearing for extension of an elongate urine sack or urine tube.

Figure 4A:
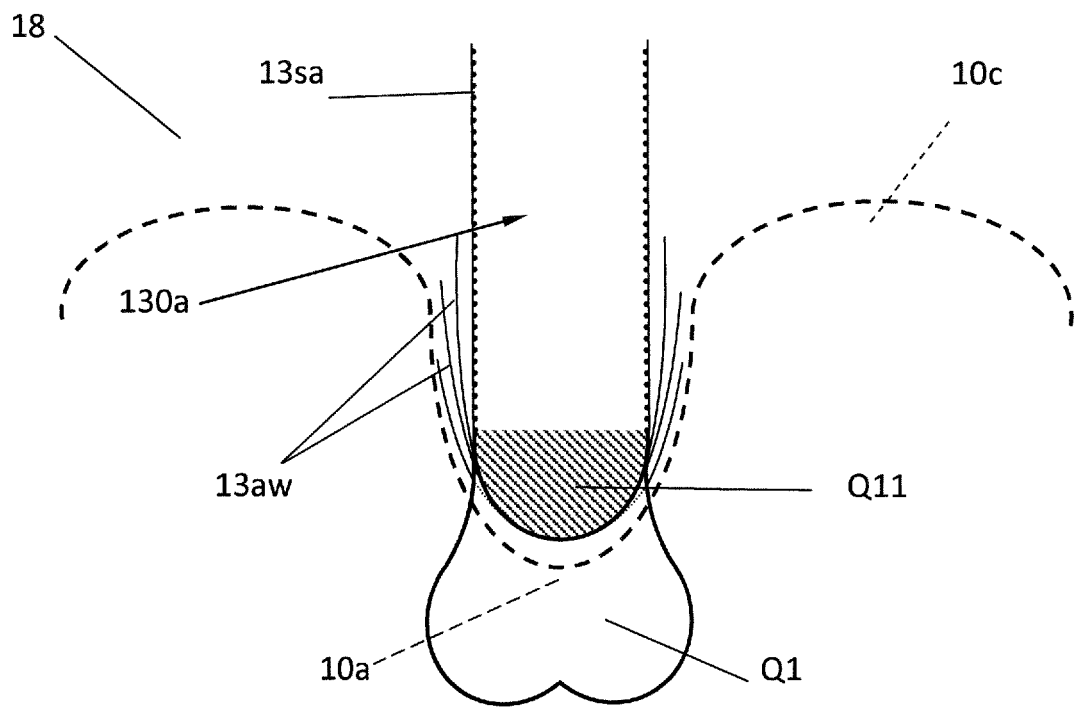
FIGS. 4A and 4B, which are provided for comparison, are respectively schematic views showing a longitudinal straight line opening and a V-shaped line opening tightly enclosing around a rear root portion of a scrotum (in a sectioned form).
Figure 4B:
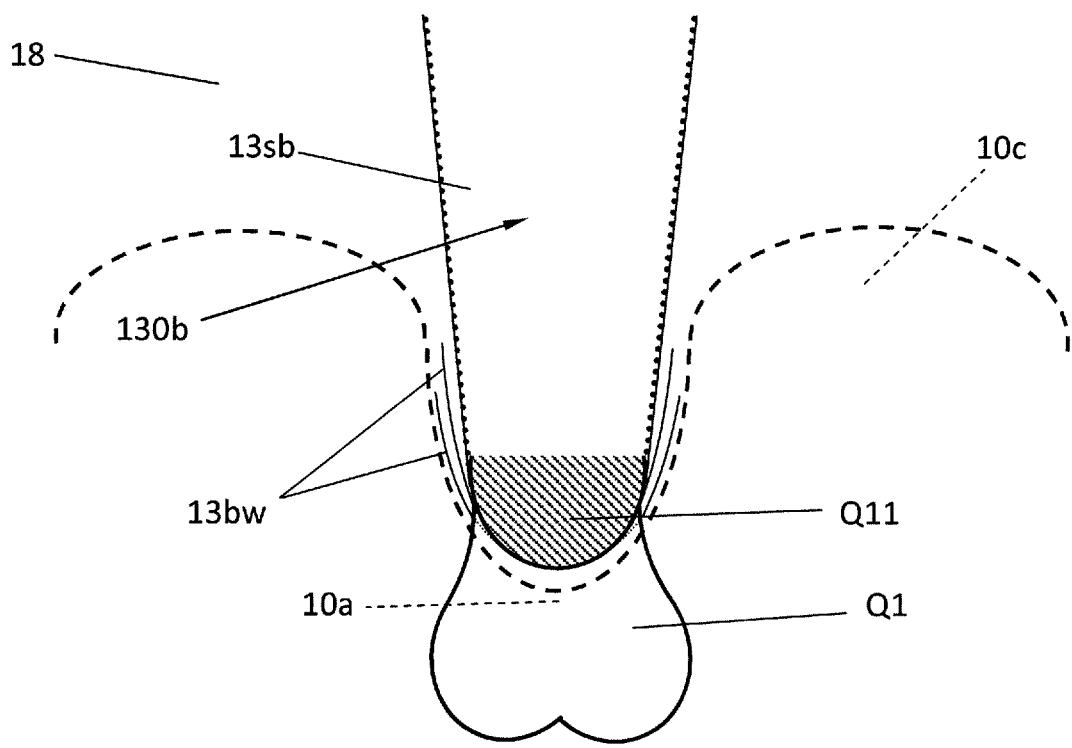
Figure 5:
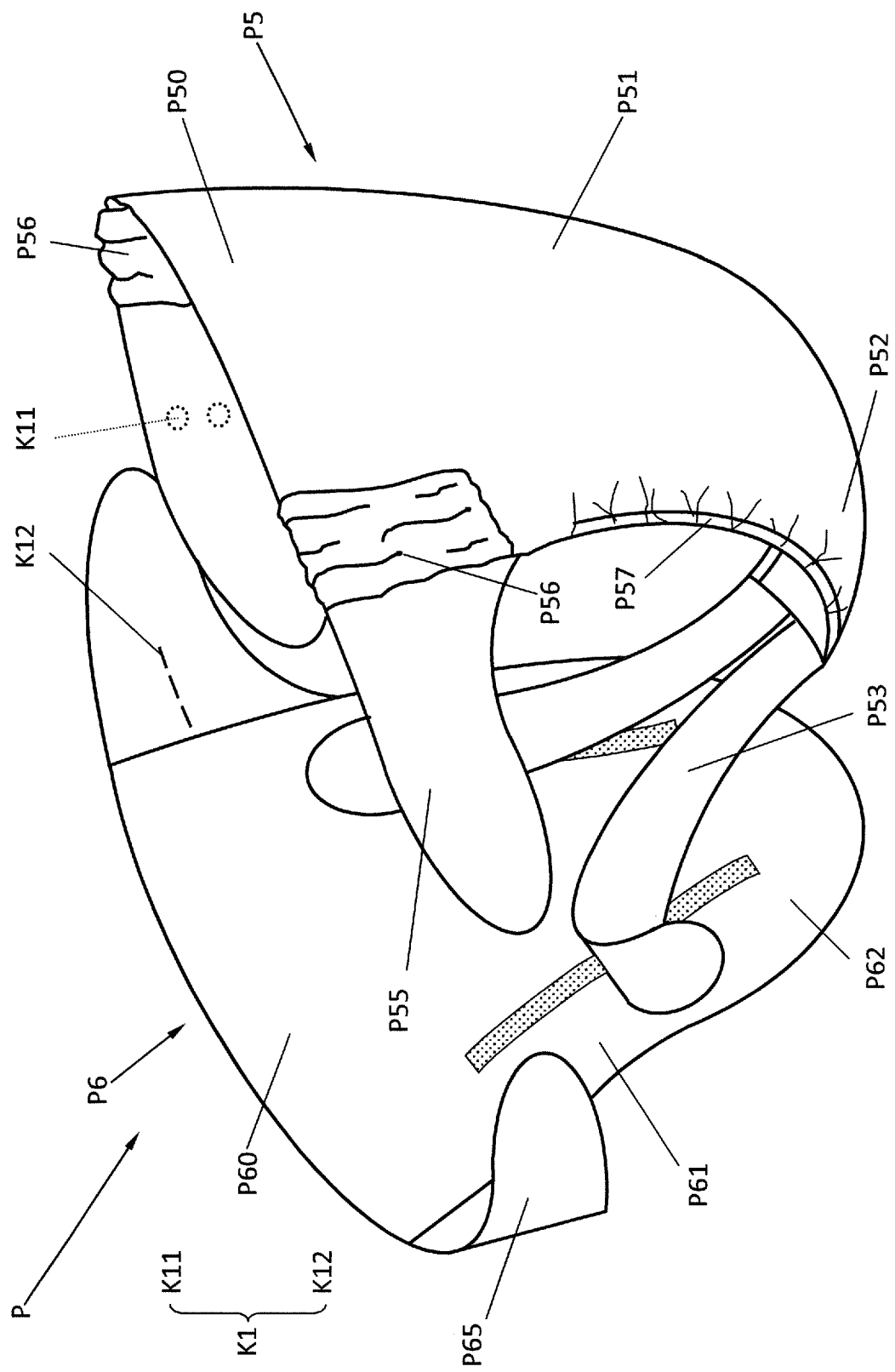
FIG. 5 is a schematic view of enclosing pants according to the present invention, showing locations of single-side-arrangement positioning fasteners on a rear pad and a front pad.
Figure 6:
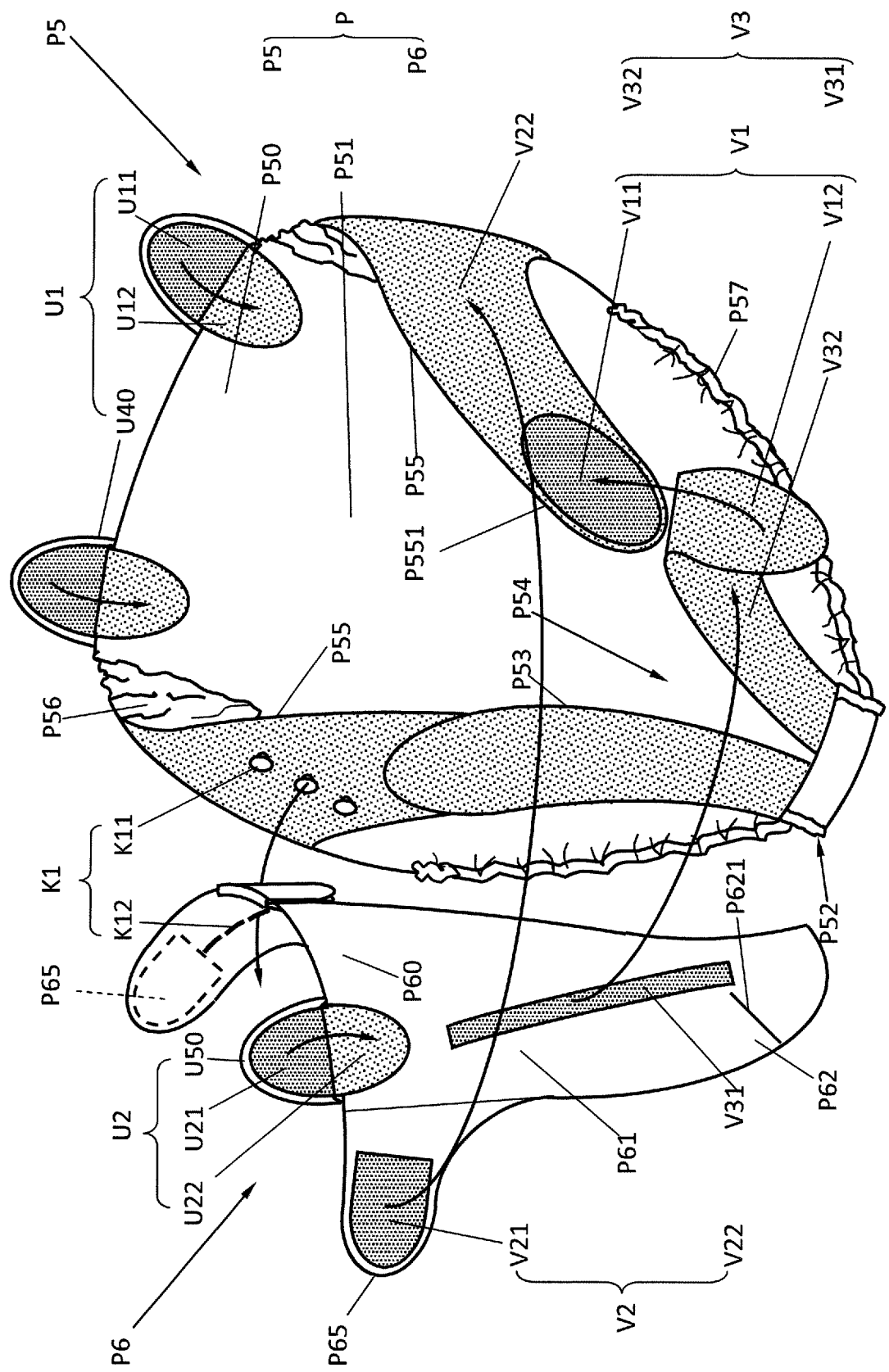
FIG. 6 is a schematic perspective view showing an arrangement of first to third fasteners on the enclosing pants.

The easy tear line opening of the absorbent article 1, 2 has a width that is smaller than the root of the scrotum and the property of the film that is soft and stretchable is used to allow a bottom of the opening to abut the rear root portion Q11 of the scrotum Q1, and to change, through being lifting and pulling, into a pliant curved configuration (see FIGS. 4A and 4B, wrinkling 13aw, 13bw naturally generated for improving or adding a barrier layer). The narrower the opening is, the more the wrinkling there will be, so as to impose a tightly enclosing configuration for isolating the external sex organ outside the absorbent article.

The two projecting portions 10c, 20c may absorb and hold watery feces flowing along the hips toward thighs. The recessed portion between the two projecting portions help isolate contact between the scrotum and the perineum. The absorbent core has a height that helps generate a gap to avoid discomfort caused by wetting and stickiness.

The opening can be made in the form of intermittently and successively arranged through holes (namely cutting marks in the form of alternating apertures and breaks) or successively arranged interrupted linear cutting slits (namely a blade cutting mark) or markings of hot melting and pressing.

The above absorbent article may include a flexible fastener tape 161, 261, 361 provided on a middle-upper portion of an inside surface of the rear lifting film for rolling up and fixing the absorbent article before disposal.

FIGS. 5-10 show an embodiment of enclosing pants P according to the present invention, comprising a rear pad P5 that comprises a rear waist section P50, a rear hip section P51, a crotch section P52, elastic extension/contraction sections P56 arranged on the rear waist section at locations adjacent to left and right sides respectively, rear wing sections P55 arranged at the left and right sides of the rear waist section and each including an extension section P551 (such that the rear wing sections can be pulled to extend, by means of the extension/contraction sections, toward left and right belly portions of the wearer), lifting and looping sections P53 respectively arranged leftward and rightward and connected to a front end of the crotch section for respectively corresponding to and engaging with the extension sections P551, a central opening section P54 defined by the lifting and looping sections collectively, and thigh circumference extension/contraction edges P57 respectively arranged at edges of left and right sides of the rear hip section and the crotch section; and a front pad P6, which comprises a front waist section P60, a front belly section P61, a down-extension section P62 that covers a male external sex organ (and is alternatively or selectively provided, through sewing, with two fold lines P621 for pliantly attaching to the privates), and front wing sections P65 attached to left and right sides of the front waist section and respectively corresponding to and engaging with the rear wing sections, wherein the extension sections and the lifting and looping sections are engageable with and attached to each other by means of first fasteners V1, in a detachable manner, on left and right belly portions of the wearer (the rear pad being independently or separately wearable); the rear wing sections and the front wing sections that are corresponding to each other are engageable with and attached to each other by means of second fasteners V2, in a detachable manner; the lifting and looping sections and the front pad are engageable with and attached to each other by means of third fasteners V3, in a detachable manner, on the left and right belly portions of the wearer; the opening section P54 enable outward extension and exposure of the male external sex organ and the front pad is lifted open for fixing a urine tube S or installing a urine sack T, or for adjusting a spacing distance between the third fasteners V3 on the left and right sides.

In other embodiments, the enclosing pants further comprise one group of single-side-arrangement positioning fasteners K1 (FIGS. 6 and 7) for engagement and positioning in a detachable manner (in a first time of wearing, the front pad is set on and covers the belly of the wearer and adjustment is made for horizontal and vertical positions, and the closest one set of fasteners, once set in engagement don't take it detach), wherein the positioning fasteners K1 comprise buttons K11 arranged to line up in a top-bottom direction on an outside surface of one of the rear wing sections and slits K12 formed in a corresponding one of the front wing sections as being arranged to line up in a left-right direction for receiving the buttons to selectively pass therethrough; or alternatively, positioning fasteners K2 (FIG. 9) comprising a hook K21 arranged on the inside surface of one of the front wing plates and multiple ring rows or loop rows arranged on the outside surface of a corresponding one of rear wing plates and lining up in a top-down direction for selectively receiving the hook to pass therethrough, the ring rows comprising multiple rings K22 arranged to line up in a left-right direction; or alternatively, a positioning fastener K3 (FIG. 10) comprising ring buckles K32 arranged on the outside surface of one of the rear wing plates to line up in a top-bottom direction and a buckle strap K31 arranged on the inside surface of a corresponding one of the front wing plates for selectively extending through the ring buckles.

The first fastener V1 can be a hook-and-loop fastener, of which one of a male part V11 and a female part V12 is mounted on an inside surface of the lifting and looping sections, and the other one of the male part and the female part is mounted on the outside surface of the extension sections of the rear wing sections. the second fastener V2 can be a hook-and-loop fastener, of which one of a male part V21 and female parts V22 is mounted on the inside surface of the front wing sections, and the other of the male part and the female part is mounted on the outside surface of the rear wing sections. the third fastener V3 can be a hook-and-loop fastener, of which one of a male part V31 and female parts V32 is mounted on the outside surface of the lifting and looping section, and the other of the male part and female part is mounted on the inside surface of the extension section of the front pad.

Alternatively, the first and second fastener can be of multiple snap touch fasteners.

In another embodiment (FIG. 9), the inside surfaces of the rear hip section and the lifting and looping section are provided with a hook-and-loop fastener male part Y for attaching to and engaging with a nonwoven-fabric surface layer of the absorbent article 2.

Figure 11A:
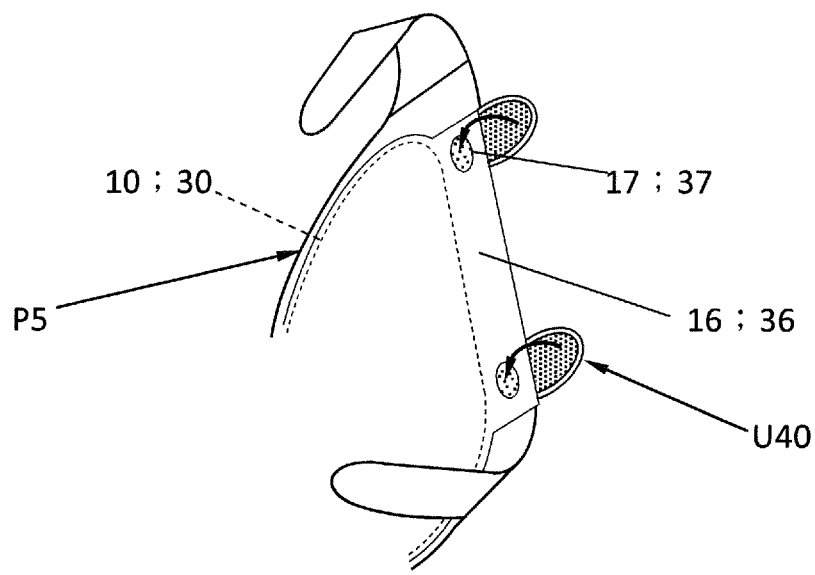
FIGS. 11A, 11B, and 11C, which are provided for comparison with each other, are schematic views respectively showing a rear fastening unit fastened to locations on an inner side, an upper side, and an outer side of a rear waist section.
Figures 11B, 11C:
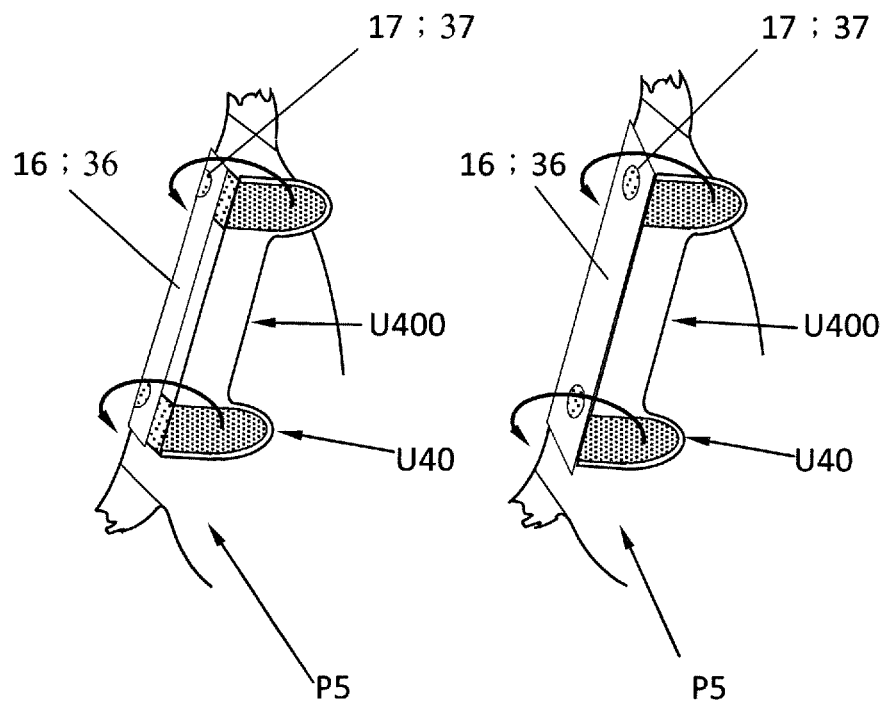
Figure 16A:
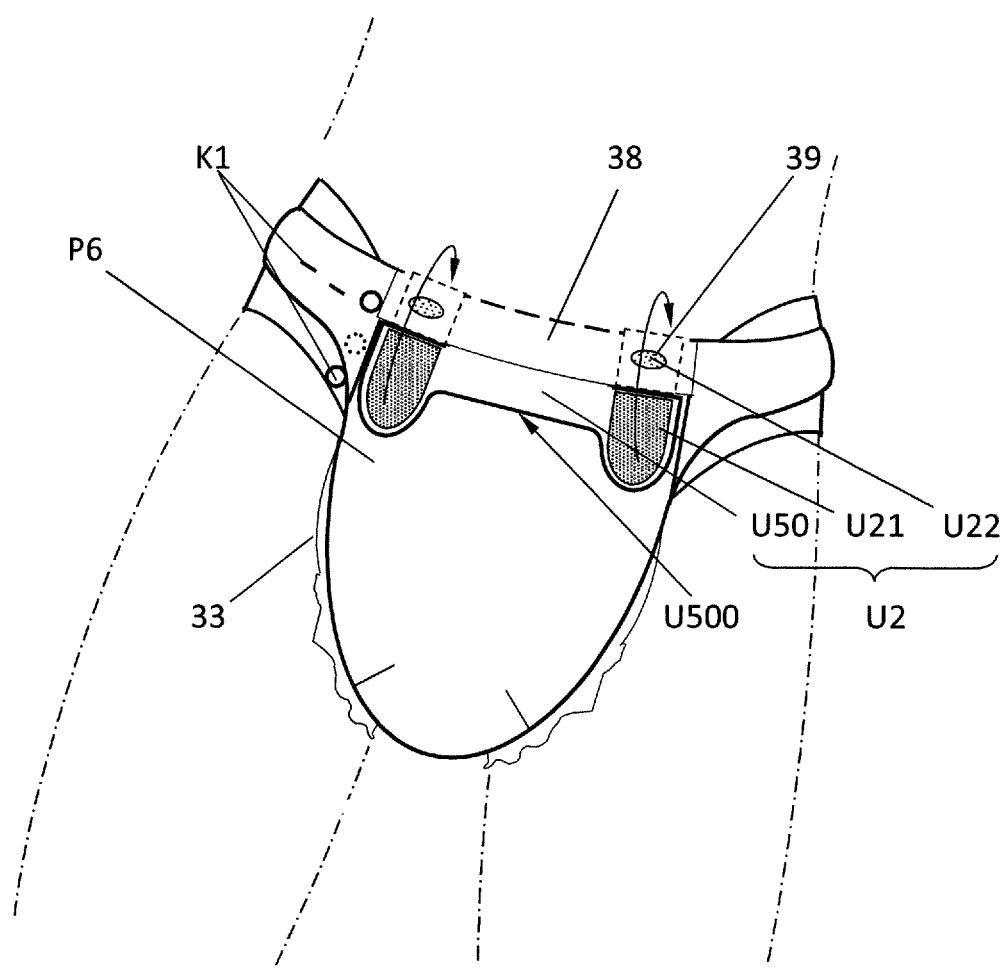
FIGS. 16A and 16B, which are provided for comparison, are schematic views respectively showing, conditions anterior to and posterior to fastening of a front fastening unit during wearing the enclosing pants and the shielding absorbent article.
Figure 16B:
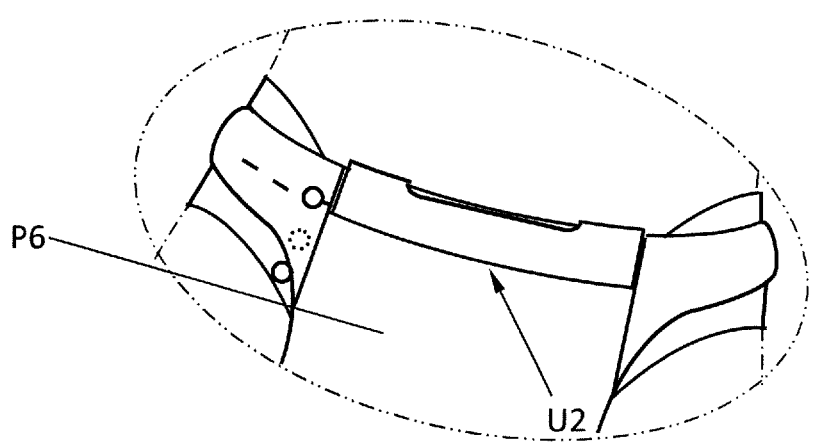

In some embodiments, the enclosing pants further comprises a front fastening unit U2 and a rear fastening unit U1 that are arranged opposite to each other on that front waist section P60 and that rear waist section P50, the front fastening unit U2 and a rear fastening unit U1 that are foldable from an outside surface onto an inside surface for fastening and each comprising two hook-and-loop fastener male parts U11, U21 symmetrically arranged on the outside surface and foldable from outside toward inside for fastening and two hook-and-loop fastener female parts U12, U22 associated therewith are respectively set on and cover, in a corresponding manner, the inside surface and the outside surface; and a connection portion U40, U50 arranged on the outside surface in a horizontal direction at a location below the hook-and-loop fastener female parts U12, U22, wherein the connection portion is provided, on left and right end parts of an inside surface thereof, with the hook-and-loop fastener male parts respectively; in a modified embodiment, the connection portion further a recessed portion U400, U500 being provided between the recessed portion adapted to avoid contacting and staining by fecal matter. Reference being had to FIGS. 11A, 11B, and 11C, the rear fastening unit is fastenable to the apertures 17, 37 of a rear lifting film 16, 36 at different locations of the rear waist section; and FIGS. 16A and 16B are schematic views respectively showing conditions anterior to and posterior to fastening of the front fastening unit.

Figure 17:
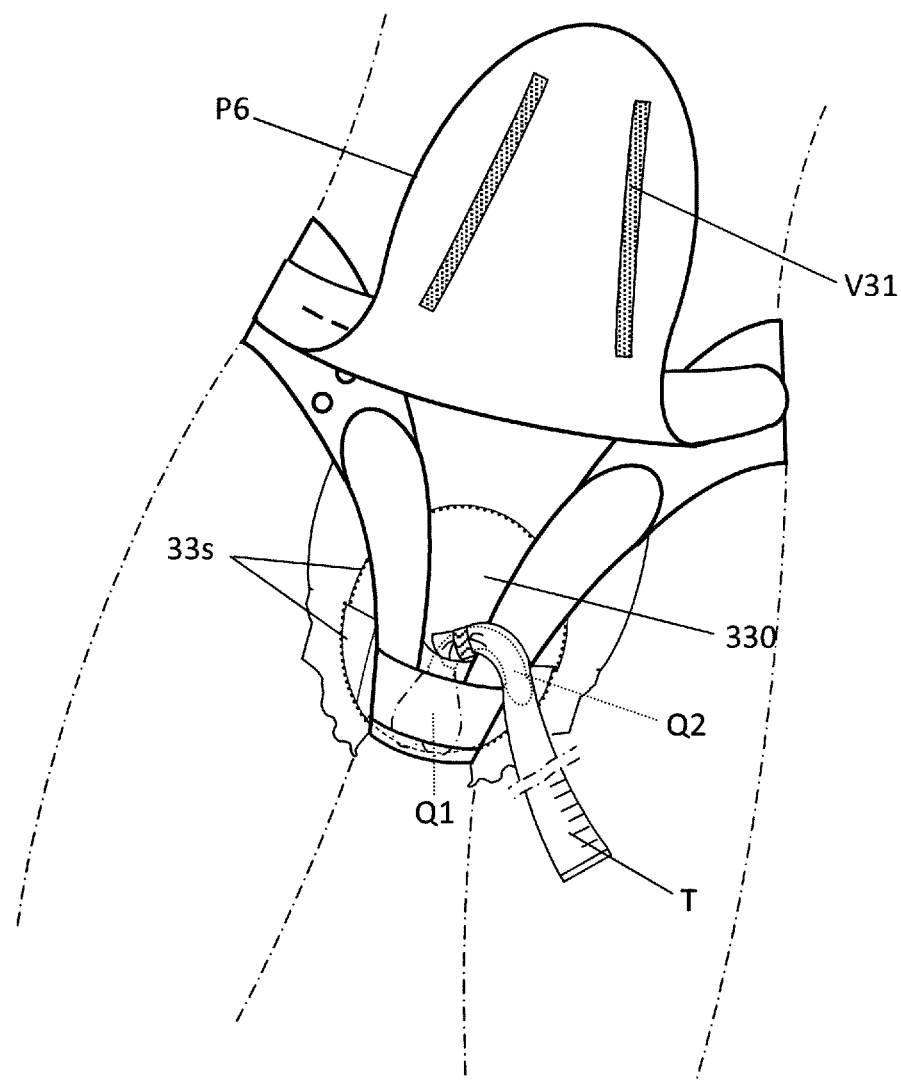
FIG. 17 is a schematic view showing a condition after a urine sack is installed through lifting open a front pad that has been closed for covering during wearing the enclosing pants and the shielding absorbent article.

In a modified embodiment, the front end of the crotch section is extended to a position corresponding to a body surface of a wearer at an upper end of the pubic bone to form an upward-extending section P52H, and the outside surface is provided with a separation portion V33 of the third fastener female part for fastening with a lower portion of the male part, this being applicable to the shielding absorbent article (FIGS. 10 and 17) to prevent the scrotum Q1 located inside the crotch section from being compressed.

Figure 12A:
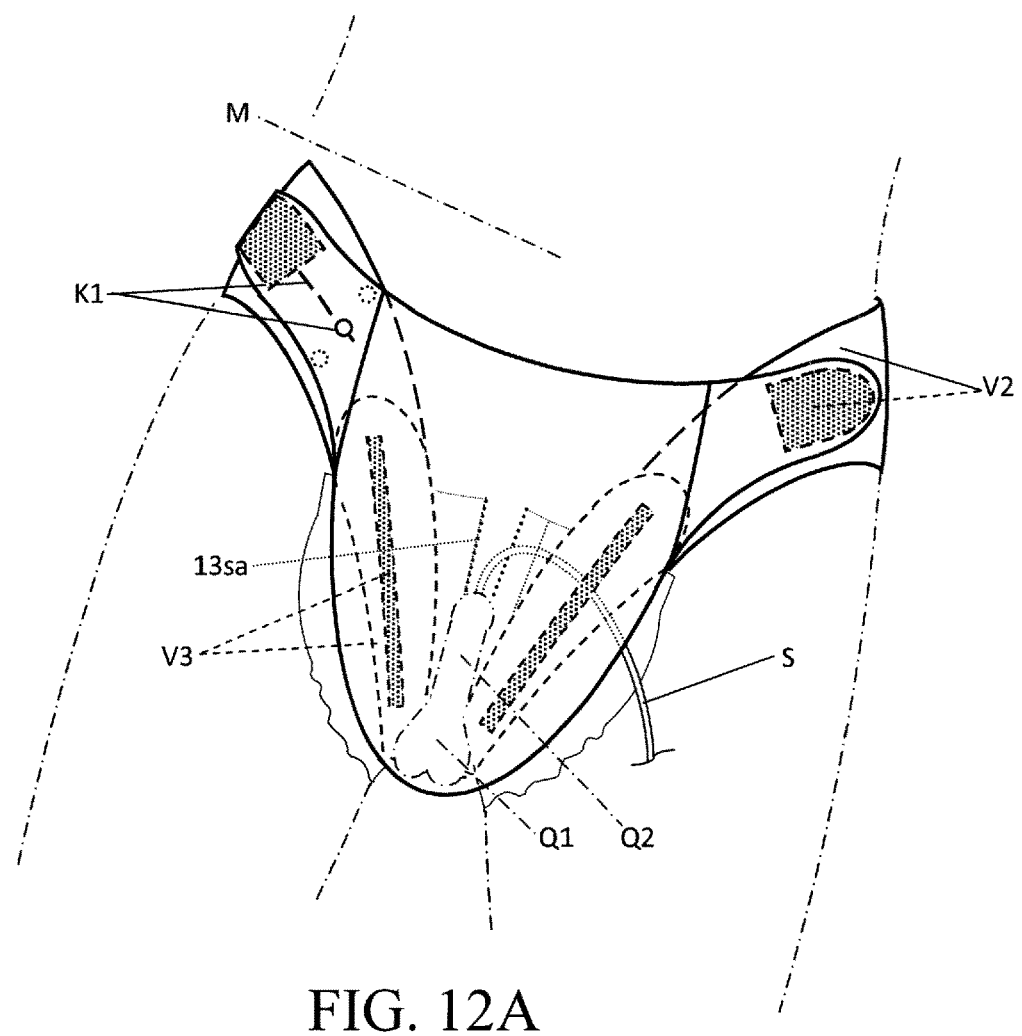
FIGS. 12A and 12B, which are provided for comparison, are schematic views respectively showing a male and a female wearing the aperture-included isolating absorbent article, where a urine tube is retained at a position between a male part and a female part of the third fastener.
Figure 12B:
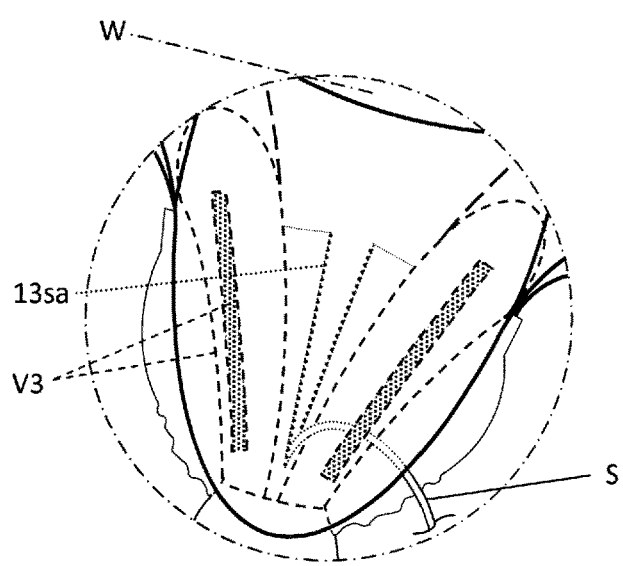

Taking the absorbent article 1 and the enclosing pants that is provided with the rear fastening unit U1 (in a condition of being properly positioned and fastened) as an example for explanation of a method for wearing a combination of the two, the method comprises the following steps: (A) expanding the enclosing pants P and placing the absorbent article 1 therein such that the easy tear line is higher than the crotch section by at least 1 cm, positioning the rear lifting film aperture 17 between the male part U11 and the female part U12 of the rear fastening unit U1 and then carrying out fastening for fixing; (B) placing the rear pad P5 including the absorbent article 1 on a rear side of the hips of a wearer, tearing open the easy tear line and having a bottom of the opening abutting the rear root portion Q11 of the scrotum Q1; (C) pulling together and overlapping the extension section P551 of one side and the front lifting section 18 that is expanded under the crotch and including the aperture 19, holding with one hand and pulling and lifting the lifting and looping section 53 of the same side from below the crotch to have the first fastener V1 fastened inside the aperture 19 and repeating the above operation for the other side, such that the opening is set tightly around the rear root portion of the scrotum; (D) fastening the second fastener V2 on the non-positioning side to have the front pad P6 covering the belly of the wearer; (E) lifting open the front pad, installing a urine tube S or a urine sack T on a penis Q2 and then placing the urine tube S or the urine sack T at a target position on the female part V32 of the third fastener V3 at one side (FIGS. 12A, 12B, and 17) or placing the urine sack between the female parts on the two sides (FIGS. 14A and 14B) and covering the front pad back and fastening the third fastener.

Step (C) can be simplified, after acquaintance with the fastening position, as follows: (C) one hand holding the extension section of the rear wing section at one side and the other hand pulling and lifting the lifting and looping section and the front lifting section including the aperture 19 simultaneously for overlapping on the extension section and having the first fastener fastened; and repeating the above operation for the other side to have the bottom of the opening abutting the rear root portion of the scrotum.

Figure 15:
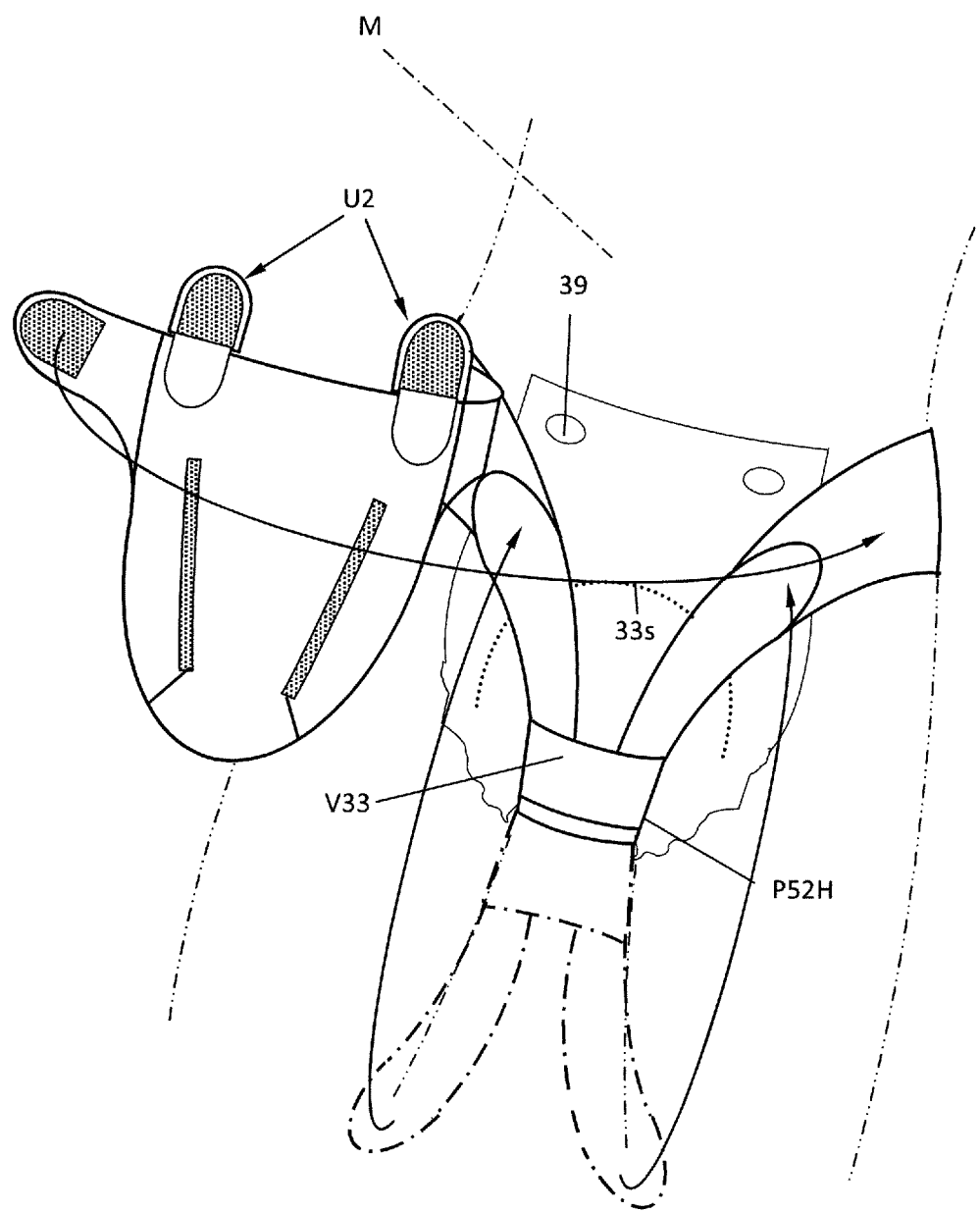
FIG. 15 is a schematic view showing a condition anterior to closing a front pad, after being positioned, during wearing the enclosing pants and the shielding absorbent article.

Further taking the absorbent article 3 and the enclosing pants having the upward-extending section P52H extended from the crotch section and the separation portion V33 (in a condition of being properly positioned and fastened) as an example for explanation of a method for wearing a combination of the two, the method comprises the following steps: (a) expanding the rear pad and placing the absorbent article therein such that the rear lifting film aperture is located between the male part and the female part of the rear fastening unit and then carrying out fastening for fixing; (b) placing the rear pad including the absorbent article on a rear side the hips of a wearer; (c) pulling together and overlapping the extension section of one side and the lifting and looping section under the crotch and having the first fastener fastened outside the absorbent article (FIG. 15) and repeating the above operation for the other side; (d) fastening the second fastener on the non-positioning side and then placing the front lifting section aperture between the male part U21 and the female part U22 of the front fastening unit U2 and carrying out fastening for fixing; (e) lifting open the front pad and releasing the first fastener, tearing apart the easy tear line and folding downward to expose the penis and then fastening back the first fastener; and (f) installing a urine sack on the penis and located between the two lifting and looping sections (FIGS. 14A and 14B) or placing at a target position on the female part of the third fastener of a lifting and looping section and setting back the front pad for covering and fastening the third fastener.

Figure 9:
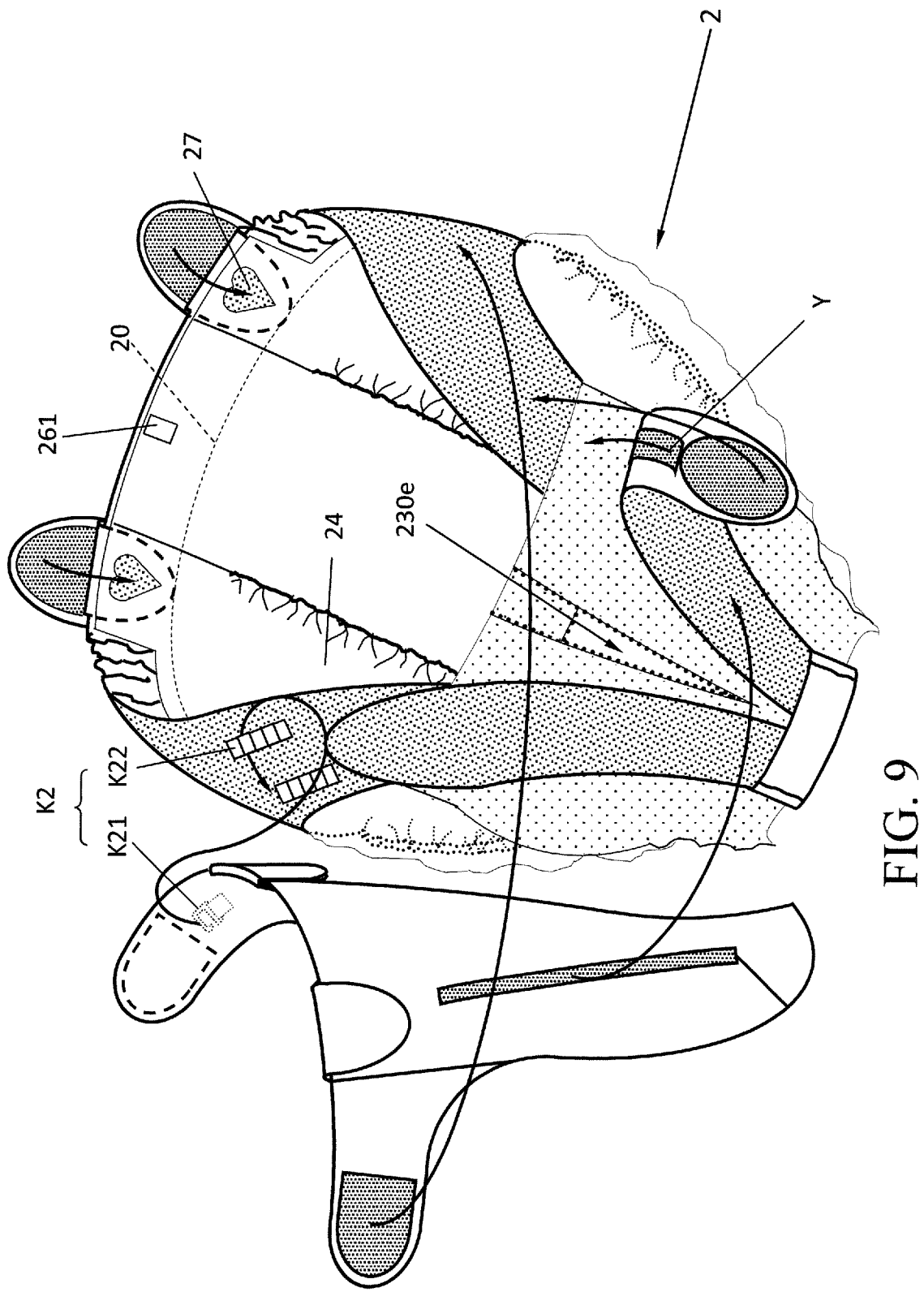
FIG. 9 is a schematic perspective view showing the enclosing pants being disposed with the nonwoven-fabric-surface-layer-included isolating absorbent article.

Further taking the absorbent article 2 and the enclosing pants having the hook-and-loop fastener male part Y arranged on the inside surface of the rear pad (in a condition of being properly positioned and fastened) as an example for explanation of a method for wearing a combination of the two, the method comprises the following steps: (A') expanding the enclosing pants P and placing the absorbent article 2 therein such that the easy tear line is higher than the crotch section by at least 1 cm, and having the nonwoven fabric outer surface layer 202 attached to and engaging with the hook-and-loop fastener male part Y arranged on the inside surface of the enclosing pants (FIG. 9); (B') placing the rear pad including the absorbent article on a rear side of the hips of a wearer, tearing open the easy tear line and having a bottom of the opening abutting the rear root portion of the scrotum; (C') pulling together and overlapping the extension section P551 and the lifting and looping section P53 under the crotch and fastening the first fastener, and repeating the above operation for the other side to have the opening set tightly around the rear root portion of the scrotum; (D') fastening the second fastener on the non-positioning side to have the front pad P6 covering the belly of the wearer; (E') lifting open the front pad, installing a urine sack T on the penis and placing the urine sack at a target position on the female part V32 of the third fastener of one side, or placing the urine sack T between the two female parts V32, and covering the front pad back and fastening the third fastener.

I claim:

1. An absorbent article, which is adapted to wear in combination with enclosing pants, the absorbent article comprising:
   a liquid permeable top layer, a liquid impermeable bottom layer, an absorbent core disposed between the liquid permeable top layer and the liquid impermeable bottom layer, and a leaking protection barrier extending in a longitudinal direction along left and right sides of the liquid permeable top layer;
   wherein the absorbent core at least comprises a rear hip section and a crotch section, the absorbent core having a front-side film extended to form a front lifting section, the absorbent article having a rear waist side film extended to form a rear lifting film;
   wherein the at least one aperture is provided in left and right sides, the at least one aperture allows for the male and female parts of a hook-and-loop fastener to engage for fastening and lifting;
   wherein at lease one aperture is provided in left and right sides, the at least one aperture that allows male and female parts of a hook-and-loop fastener to engage for fastening and lifting;
   wherein the aperture has a plan-view configuration that is one of a heart shape, a star shape, and geometric shapes of circle, ellipse, oval, rectangle, triangle, trapezoid, pentagon, and hexagon; and
   wherein the absorbent core comprises the rear hip section and the crotch section, wherein the absorbent core has a front end that is formed with two projecting portions adapted to respectively extend on left and right sides of an external sex organ of a male wearer, and a recessed portion that is formed between the two projecting portions and is provided, at a location corresponding to a root portion of a scrotum of the wearer, with an easy tear line that selectively defines an opening extending in a direction toward a belly of the wearer to form an isolating absorbent article.

2. The absorbent article according to claim 1, wherein the easy tear line opening is made in the form of a longitudinal straight line.

3. The absorbent article according to claim 1, wherein the easy tear line opening is made in the form of a V-shaped line having an internal angle smaller than 20°; or the easy tear line opening is of a capsule shape or an elliptic shape and having a top end connected with a longitudinal straight line, the capsule shape or the elliptic shape having a transverse minor axis having a length less than 1 cm and a the longitudinal major axis having a length of 2.5-8 cm; or the easy tear line opening is in the form of an inverted A-shaped line; or the easy tear line opening is in the form of multiple straight lines intersecting at a center point and including an upward-extending longitudinal straight line, the straight lines being tearable apart and foldable to form an elliptic shape of the opening, wherein the elliptic shape has a transverse minor axis having a length of 1.5-3 cm and a longitudinal major axis having a length of 6 cm±2 cm.

4. The absorbent article according to claim 1, wherein the absorbent core further comprises a front belly section extending from a front end of the crotch section to a height that is adapted to correspond to one half of a belly of a wearer±2 cm, wherein the front belly section comprises a film that is provided with an easy tear line that selectively defining an opening extending along an outer circumference of the front belly section of the absorbent core to form a shielding absorbent article.

5. An absorbent article, wearable in combination with enclosing pants, the absorbent article comprising a liquid permeable top layer, a liquid impermeable bottom layer, an absorbent core disposed between the liquid permeable top layer and the liquid impermeable bottom layer, and a leaking protection barrier extending in a longitudinal direction along left and right sides of the liquid permeable top layer, wherein the absorbent core comprises a rear hip section and a crotch section, the absorbent core having a front-side film extended to form a front lifting section, wherein the absorbent core has a front end that is formed with two projecting portions adapted to respectively extend on left and right sides of an external sex organ of a male wearer, and a recessed portion that is formed between the two projecting portions and is provided, at a location corresponding to a root portion of a scrotum of the wearer, with an easy tear line that selectively defines an opening extending in a direction toward a belly of the wearer to form an isolating absorbent article.

6. The absorbent article according to claim 5, wherein the bottom layer is combined with a nonwoven-fabric surface layer of fibers or a high-loft material.

7. The absorbent article according to claim 5, wherein the bottom layer has a back surface that is provided with adhesive for fixing to an inside surface of a rear pad of the enclosing pants.

8. The absorbent article according to claim 5, wherein the easy tear line opening is in the form of a longitudinal straight line.

9. The absorbent article according to claim 5, wherein the easy tear line opening is in the form of a V-shaped line having an internal angle smaller than 20°; or the easy tear line opening is of a capsule shape or an elliptic shape and having a top end connected with a longitudinal straight line, the capsule shape or the elliptic shape having a transverse minor axis having a length less than 1 cm and a the longitudinal major axis having a length of 2.5-8 cm; or the easy tear line opening is in the form of an inverted A-shaped line; or the easy tear line opening is in the form of multiple straight lines intersecting at a center point and including an upward-extending longitudinal straight line, the straight lines being tearable apart and foldable to form an elliptic shape of the opening, wherein the elliptic shape has a transverse minor axis having a length of 1.5-3 cm and a longitudinal major axis having a length of 6 cm±2 cm.

10. The absorbent article according to claim 6, wherein the easy tear line opening is in the form of a longitudinal straight line; or the easy tear line opening is in the form of a V-shaped line having an internal angle smaller than 20°; or the easy tear line opening is of a capsule shape or an elliptic shape and having a top end connected with a longitudinal straight line, the capsule shape or the elliptic shape having a transverse minor axis having a length less than 1 cm and a the longitudinal major axis having a length of 2.5-8 cm; or the easy tear line opening is in the form of an inverted A-shaped line; or the easy tear line opening is in the form of multiple straight lines intersecting at a center point and including an upward-extending longitudinal straight line, the straight lines being tearable apart and foldable to form an elliptic shape of the opening, wherein the elliptic shape has a transverse minor axis having a length of 1.5-3 cm and a longitudinal major axis having a length of 6 cm±2 cm.

11. Enclosing pants, which are adapted to wear in combination with an absorbent article, the enclosing pants comprising:
 a rear pad, which comprises a rear waist section, a rear hip section, a crotch section extending from a lower end of the rear hip section, elastic extension/contraction sections arranged on the rear waist section at locations adjacent to left and right sides, respectively, rear wing sections connected to the left and right sides of the rear waist section respectively and each having an extension section, two lifting and looping sections respectively arranged leftward and rightward and connected to a front end of the crotch section for respectively corresponding to the extension sections, a central opening section defined by the two lifting and looping sections collectively, and thigh circumference extension/contraction edges respectively arranged at edges of left and right sides of the rear hip section and the crotch section; and
 a front pad, which comprises a front waist section, a front belly section, a down-extension section that is adapted to cover a male external sex organ, and front wing sections arranged at left and right sides of the front waist section and respectively corresponding to the rear wing sections;
 wherein the extension sections and the lifting and looping sections are engageable with and attached to each other by means of a first fastener, in a detachable manner, on left and right belly portions of the wearer; the rear wing sections and the front wing sections are engageable with and attached to each other by means of second fasteners, in a detachable manner; and the lifting and looping sections and the front pad are engageable with and attached to each other by means of third fasteners, in a detachable manner, on the left and right belly portions of the wearer, wherein the rear pad and the front pad are combinable to form a pair of enclosing pants and an opening section is formed to correspond to an opening of the absorbent article to expose the male external sex organ.

12. The enclosing pants according to claim 11, further comprising one positioning fastener group, which comprises buttons that are provided on an outside surface of one of the rear wing sections and arranged to line up in a top-bottom direction and slits formed in a corresponding one of the front wing sections and arranged to line up in a left-right direction.

13. The enclosing pants according to claim 11, wherein the first fastener comprises a hook-and-loop fastener, which has a male part and a female part of which one of is arranged on an inside surface of the lifting and looping sections, and a second done of the male part and the female part is arranged on an outside surface of the extension sections of the rear wing sections; the second fastener comprises a hook-and-loop fastener, which has a male part and a female part of which one of is arranged on an inside surface of the front wing sections, and the other of the male part and the female part is arranged on an outside surface of the rear wing sections; the third fastener comprises a hook-and-loop fastener, which has a male part and a female part of which the one of is arranged on an outside surface of the lifting and looping sections and the other of the male part and a female part arranged on an inside surface of the front pad.

14. The enclosing pants according to claim 11, wherein an inside surface of the rear hip section and the lifting and looping sections is provided with a hook-and-loop fastener male part to receive a nonwoven-fabric surface layer of the absorbent article to attach thereto and engage therewith.

15. The enclosing pants according to claim 11, further comprising a front fastening unit and a rear fastening unit that are arranged opposite to each other on that front waist section and a rear waist section, a front fastening unit and a rear fastening unit that are foldable from an outside surface onto an inside surface for fastening and each comprising two hook-and-loop fastener male parts symmetrically arranged on the outside surface and foldable from outside toward inside for fastening and two hook-and-loop fastener female parts associated therewith are respectively set on and cover, in a corresponding manner, the inside surface and the outside surface; and a connection portion arranged on the outside surface in a horizontal direction at a location below the hook-and-loop fastener female parts, wherein the connection portion is provided, on left and right end parts of an inside surface thereof, with the hook-and-loop fastener male parts respectively.

16. The enclosing pants according to claim 11, wherein the connection portion further comprising a recessed portion being provided between the two male parts adapted to avoid contacting and staining by fecal matter.

17. The enclosing pants according to claim 14, wherein the crotch section has a front end extended to a position adapted to correspond to a body surface of a wearer at an upper end of the pubic bone to form an upward-extending section, and an outside surface is provided with a separation portion of the third fastener female part.

18. A method for wearing a combination of an absorbent article and enclosing pants, wherein the absorbent article comprises:
a liquid permeable top layer, a liquid impermeable bottom layer, an absorbent core disposed between the liquid permeable top layer and the liquid impermeable bottom layer, and a leaking protection barrier extending in a longitudinal direction along left and right sides of the liquid permeable top layer, wherein the absorbent core at least comprises a rear hip section and a crotch section, the absorbent core having a front-side film extended to form a front lifting section, the absorbent article having a rear waist side film extended to form a rear lifting film, wherein the rear lifting film is provided, in left and right sides, with at least one aperture that allows male and female parts of a hook-and-loop fastener to engage for fastening and lifting and the front lifting section is provided, in left and right sides, with at least one aperture that allows male and female parts of a hook-and-loop fastener to engage for fastening and lifting, wherein the absorbent core comprises the rear hip section and the crotch section, wherein the absorbent core has a front end that is formed with two projecting portions adapted to respectively extend on left and right sides of an external sex organ of a male wearer, and a recessed portion that is formed between the two projecting portions and is provided, at a location corresponding to a root portion of a scrotum of the wearer, with an easy tear line that selectively defines an opening extending in a direction toward a belly of the wearer to form an isolating absorbent article;
the enclosing pants comprising a rear pad, which comprises a rear waist section, a rear hip section, a crotch section extending from a lower end of the rear hip section, elastic extension/contraction sections arranged on the rear waist section at locations adjacent to left and right sides, respectively, rear wing sections connected to the left and right sides of the rear waist section respectively and each having an extension section, two lifting and looping sections respectively arranged leftward and rightward and connected to a front end of the crotch section for respectively corresponding to the extension sections, a central opening section defined by the two lifting and looping sections collectively, and thigh circumference extension/contraction edges respectively arranged at edges of left and right sides of the rear hip section and the crotch section; a front pad, which comprises a front waist section, a front belly section, a down-extension section that is adapted to cover a male external sex organ, and front wing sections arranged at left and right sides of the front waist section and respectively corresponding to the rear wing sections; and one positioning fastener group, which is arranged on one of the rear wing sections and a corresponding one of the front wing sections for selectively engaging with and fastening to each other, in a detachable manner, for positioning;
wherein the extension sections and the lifting and looping sections are engageable with and attached to each other by means of a first fastener, in a detachable manner, on left and right belly portions of the wearer; the rear wing sections and the front wing sections are engageable with and attached to each other by means of second fasteners, in a detachable manner; and the lifting and looping sections and the front pad are engageable with and attached to each other by means of third fasteners, in a detachable manner, on the left and right belly portions of the wearer, wherein the rear pad and the front pad are combinable to form a pair of enclosing pants and an opening section is formed to correspond to an opening of the absorbent article to expose the male external sex organ;
the enclosing pants further comprising a front waist section and a rear waist section that are arranged opposite to each other, a front fastening unit and a rear fastening unit that are foldable from an outside surface onto an inside surface for fastening, the front fastening unit and the rear fastening unit each comprising two hook-and-loop fastener male parts symmetrically arranged on the outside surface and foldable from outside toward inside for fastening and female parts associated therewith being respectively set on and covering, in a corresponding manner, the inside surface and the outside surface, and a connection portion arranged on the outside surface in a horizontal direction at a location below the female parts, wherein the connection portion is provided, on left and right end parts of an inside surface thereof, with the male parts respectively;
the method for wearing the combination of the absorbent article and the enclosing pants being applicable in a condition where the enclosing pants are positioned and fastened, comprising the following steps: (A) expanding the enclosing pants and placing the absorbent article therein such that the easy tear line is higher than the crotch section by at least 1 cm, positioning the rear lifting film aperture between the male part and the female part of the rear fastening unit and then carrying out fastening for fixing; (B) placing the rear pad including the absorbent article on a rear side of the hips of a wearer, tearing open the easy tear line and having a bottom of the opening abutting the rear root portion of the scrotum; (C) pulling together and overlapping the extension section of one side and the front lifting section that is expanded under the crotch and including the aperture, holding with one hand and pulling and lifting the lifting and looping section of the same side from below the crotch to have the first fastener fastened inside the aperture and repeating the above operation for the other side, such that the opening is set tightly around the rear root portion of the scrotum; (D) fastening the second fastener on the non-positioning side to have the front pad covering the belly of the wearer; (E) lifting open the front pad, installing a urine tube or a urine sack on a penis and then placing the urine tube or the urine sack at a target position on the female part of the third fastener at one side or placing the urine sack between two female parts and covering the front pad back and fastening the third fastener.

19. A method for wearing a combination of an absorbent article and enclosing pants, wherein the absorbent article comprises:

a liquid permeable top layer, a liquid impermeable bottom layer, an absorbent core disposed between the liquid permeable top layer and the liquid impermeable bottom layer, and a leaking protection barrier extending in a longitudinal direction along left and right sides of the liquid permeable top layer, wherein the absorbent core at least comprises a rear hip section and a crotch section, the absorbent core having a front-side film extended to form a front lifting section, the absorbent article having a rear waist side film extended to form a rear lifting film, wherein the rear lifting film is provided, in left and right sides, with at least one aperture that allows male and female parts of a hook-and-loop fastener to engage for fastening and lifting and the front lifting section is provided, in left and right sides, with at least one aperture that allows male and female parts of a hook-and-loop fastener to engage for fastening and lifting, the absorbent core further comprises a front belly section extending from a front end of the crotch section to a height that is adapted to correspond to one half of a belly of a wearer±2 cm, wherein the front belly section comprises a film that is provided with an easy tear line that selectively defining an opening extending along an outer circumference of the front belly section of the absorbent core to form a shielding absorbent article;

the enclosing pants comprising a rear pad, which comprises a rear waist section, a rear hip section, a crotch section extending from a lower end of the rear hip section, elastic extension/contraction sections arranged on the rear waist section at locations adjacent to left and right sides, respectively, rear wing sections connected to the left and right sides of the rear waist section respectively and each having an extension section, two lifting and looping sections respectively arranged leftward and rightward and connected to a front end of the crotch section for respectively corresponding to the extension sections, a central opening section defined by the two lifting and looping sections collectively, and thigh circumference extension/contraction edges respectively arranged at edges of left and right sides of the rear hip section and the crotch section; a front pad, which comprises a front waist section, a front belly section, a down-extension section that is adapted to cover a male external sex organ, and front wing sections arranged at left and right sides of the front waist section and respectively corresponding to the rear wing sections; and one positioning fastener group, which is arranged on one of the rear wing sections and a corresponding one of the front wing sections for selectively engaging with and fastening to each other, in a detachable manner, for positioning;

wherein the extension sections and the lifting and looping sections are engageable with and attached to each other by means of a first fastener, in a detachable manner, on left and right belly portions of the wearer; the rear wing sections and the front wing sections are engageable with and attached to each other by means of second fasteners, in a detachable manner; and the lifting and looping sections and the front pad are engageable with and attached to each other by means of third fasteners, in a detachable manner, on the left and right belly portions of the wearer, wherein the rear pad and the front pad are combinable to form a pair of enclosing pants and an opening section is formed to correspond to an opening of the absorbent article to expose the male external sex organ, and the crotch section has a front end extended to a position adapted to correspond to a body surface of a wearer at an upper end of the pubic bone to form an upward-extending section, and an outside surface is provided with a separation portion of the third fastener female part;

the enclosing pants further comprising a front waist section and a rear waist section that are arranged opposite to each other, a front fastening unit and a rear fastening unit that are foldable from an outside surface onto an inside surface for fastening, the front fastening unit and the rear fastening unit each comprising two hook-and-loop fastener male parts symmetrically arranged on the outside surface and foldable from outside toward inside for fastening and female parts associated therewith being respectively set on and covering, in a corresponding manner, the inside surface and the outside surface, and a connection portion arranged on the outside surface in a horizontal direction at a location below the female parts, wherein the connection portion is provided, on left and right end parts of an inside surface thereof, with the male parts respectively;

the method for wearing the combination of the absorbent article and the enclosing pants being applicable in a condition where the enclosing pants are positioned and fastened, comprising the following steps: (a) expanding the rear pad and placing the absorbent article therein such that the rear lifting film aperture is located between the male part and the female part of the rear fastening unit and then carrying out fastening for fixing; (b) placing the rear pad including the absorbent article on the hips of a wearer; (c) pulling together and overlapping the extension section of one side and the lifting and looping section under the crotch and having the first fastener fastened outside the absorbent article and repeating the above operation for the other side; (d) fastening the second fastener on the non-positioning side and then placing the front lifting section aperture between the male part and the female part of the front fastening unit and carrying out fastening for fixing; (e) lifting open the front pad and releasing the first fastener, tearing apart the easy tear line and folding downward to expose the penis and then fastening back the first fastener; and (f) installing a urine sack on the penis and located at a target position on the female part of the third fastener at one side and setting back the front pad for covering and fastening the third fastener.

20. A method for wearing a combination of an absorbent article and enclosing pants, wherein the absorbent article comprises:

a liquid permeable top layer, a liquid impermeable bottom layer, an absorbent core disposed between the liquid permeable top layer and the liquid impermeable bottom layer, and a leaking protection barrier extending in a longitudinal direction along left and right sides of the liquid permeable top layer, wherein the absorbent core comprises a rear hip section and a crotch section, the absorbent core having a front-side film extended to form a front lifting section, wherein the absorbent core has a front end that is formed with two projecting portions adapted to respectively extend on left and right sides of an external sex organ of a male wearer, and a recessed portion that is formed between the two projecting portions and is provided, at a location corresponding to a root portion of a scrotum of the wearer, with an easy tear line that selectively defines an opening extending in a direction toward a belly of the wearer to form an isolating absorbent article, the bottom layer being further combined with a nonwoven-fabric surface layer of fibers or a high-loft material;

the enclosing pants comprising:

a rear pad, which comprises a rear waist section, a rear hip section, a crotch section extending from a lower end of the rear hip section, elastic extension/contraction sections arranged on the rear waist section at locations adjacent to left and right sides, respectively, rear wing sections connected to the left and right sides of the rear waist section respectively and each having an extension section, two lifting and looping sections respectively arranged leftward and rightward and connected to a front end of the crotch section for respectively corresponding to the extension sections, a central opening section defined by the two lifting and looping sections collectively, and thigh circumference extension/contraction edges respectively arranged at edges of left and right sides of the rear hip section and the crotch section, wherein an inside surface of the rear hip section and the lifting and looping sections is provided with a hook-and-loop fastener male part to receive a nonwoven-fabric surface layer of the absorbent article to attach thereto and engage therewith; and a front pad, which comprises a front waist section, a front belly section, a down-extension section that is adapted to cover a male external sex organ, and front wing sections arranged at left and right sides of the front waist section and respectively corresponding to the rear wing sections; and one positioning fastener group, which is arranged on one of the rear wing sections and a corresponding one of the front wing sections for selectively engaging with and fastening to each other, in a detachable manner, for positioning;

wherein the extension sections and the lifting and looping sections are engageable with and attached to each other by means of a first fastener, in a detachable manner, on left and right belly portions of the wearer; the rear wing sections and the front wing sections are engageable with and attached to each other by means of second fasteners, in a detachable manner; and the lifting and looping sections and the front pad are engageable with and attached to each other by means of third fasteners, in a detachable manner, on the left and right belly portions of the wearer, wherein the rear pad and the front pad are combinable to form a pair of enclosing pants and an opening section is formed to correspond to an opening of the absorbent article to expose the male external sex organ;

the method for wearing the combination of the absorbent article and the enclosing pants being applicable in a condition where the enclosing pants are positioned and fastened, comprising the following steps: (A') expanding the enclosing pants and placing the absorbent article therein such that the easy tear line is higher than the crotch section by at least 1 cm, and having the nonwoven-fabric surface layer attached to and engaging with the hook-and-loop fastener male part arranged on the inside surface of the enclosing pants; (B') placing the rear pad including the absorbent article on a rear side of the hips of a wearer, tearing open the easy tear line and having a bottom of the opening abutting the rear root portion of the scrotum; (C') pulling together and overlapping the extension section and the lifting and looping section under the crotch and fastening the first fastener, and repeating the above operation for the other side to have the opening set tightly around the rear root portion of the scrotum; (D') fastening the second fastener on the non-positioning side to have the front pad covering the belly of the wearer; (E') lifting open the front pad, installing a urine sack on the penis and placing the urine sack at a target position on the female part of the third fastener of one side, or placing the urine sack between the two female parts, and covering the front pad back and fastening the third fastener.

\* \* \* \* \*